United States Patent [19]
Korneluk et al.

[11] Patent Number: 5,919,912
[45] Date of Patent: Jul. 6, 1999

[54] MAMMALIAN IAP ANTIBODIES AND DIAGNOSTIC KITS

[75] Inventors: Robert G. Korneluk; Alexander E. MacKenzie; Stephen Baird, all of Ottawa, Canada

[73] Assignee: University of Ottawa, Ottawa, Canada

[21] Appl. No.: 08/511,485

[22] Filed: Aug. 4, 1995

[51] Int. Cl.$^6$ ............................ G01N 33/53; C07K 16/00
[52] U.S. Cl. ................................. 530/389.2; 530/388.23; 435/975; 435/7.21
[58] Field of Search ............................ 530/389, 4, 389.2, 530/388.23; 435/975, 7.21

[56] References Cited

FOREIGN PATENT DOCUMENTS

WO 94/06814   3/1994   WIPO .
WO 95/19431   7/1995   WIPO .

OTHER PUBLICATIONS

Lerner, Nature, vol. 299:592–596, Oct. 1982.
Harlow et al., Antibodies: A laboratory manual. Cold Spring Harbor Laboratory, p. 76, Aug. 1989.
Birnbaum et al., J. Virology, vol. 68:2521–2528, Apr. 1994.
H. Steller, "Mechanisms and Genes of Cellular Suicide", Science 267:1445, 1995.
Williams et al., "Apoptosis: final control point in cell biology", Trends in Cell Biology 2:263, 1992.
S. Korsmeyer, "Regulators of cell death", TIG 11:101, 1995.
Birnbaum et al., "An apoptosis–inhibiting gene from a nuclear polyhedrosis virus encoding a polypeptide with Cys/His sequence motifs", J. of Virol. 68:2521, 1994.
Crook et al., "An apoptosis–inhibiting baculovirus gene with a zinc finger–like motif", J. of Virol. 67:2168, 1993.
A. Wyllie, "Death gets a brake", Naature 369:272, 1994.
Clem et al., "Control of programmed cell death by the baculovirus genes p35 and iap", Mol. and Cell. Biology 14:5212, 1994.
Clem et al., "Prevention of apoptosis by a baculovirus gene during infection of insect cells", Science 254:1388, 1991.
Nunez et al., "The Bcl–2 family of proteins: regulators of cell death and survival", Trends in Cell Biology 4:399, 1994.
Golstein et al., "Homology between reaper and the cell death domains of Fas and TNFR1", Cell 81:185, 1995.
Clem et al., "Induction and inhibition of apoptosis by insect viruses", *Apoptosis II: The Molecular Basis of Apoptosis in Disease,* Cold Spring Harbor Laboratory Press, p. 89, 1994.
J. Kerr, "Neglected opportunities in apoptosis research", Trends in Cell Biology 5:55, 1995.
Roy et al., "The gene for neuronal apoptosis inhibitory protein is partially deleted in individuals with spinal muscular atrophy", Cell 80:167, 1995.
Osborne et al., "Essential genes that regulate apoptosis", Trends in Cell Biology 4:394, 1994.
White et al., "Genetic control of programmed cell death in drosophila", Science 264:677, 1994.
Fisher et al., "Dominant interfering Fas gene mutations impair apoptosis in a human autoimmune lymphoproliferative syndrome", Cell 81:935, 1995.
Rieux–Laucat et al., "Mutations in Fas associated with human lymphoproliferative syndrome and autoimmunity", Science 268:1347, 1995.
Katsikis et al., "Fas antigen stimulation induces marked apoptosis of T lymphocytes in human immunodeficiency virus–infected individuals", Abstract, J. Exp. Med. 1815:2029, 1995.
Muro–Cacho et al., "Analysis of apoptosis in lymph nodes of HIV–infected persons . . . ", Abstract, J. Immunol. 154:5555, 1995.
Li et al., "Induction of apoptosis in uninfected lymphocytes by HIV–1 Tat protein", Abstract, Science 268:429, 1995.
Westendorp et al., "Sensitization of T cells to CD95–mediated apoptosis by HIV–1 Tat and gp120", Nature 375:497, 1995.
Walkinshaw et al., "Induction of apoptosis in catecholamingeric PC12 cells by L–DOPA . . . ", Abstract, J. Clin. Invest. 95::2458, 1995.
Gibellini et al., "Tat–expression Jurkat cells show an increased resistance to different apoptic stimuli . . . " Abstract, Br. J. Haematol 89:24, 1995.
Martin et al., "HIV–1 infection of human CD4+ T cells in vitro . . . ", Abstract, J. Immunol. 152:330, 1994.
Terai et al., "Apoptosis as a mechanism of cell death in cultured T lymphoblasts acutely infected with HIV–1" Abstract, J. Clin. Invest. 87:1710, 1991.
Dhein et al., "Autocrine T–cells suicide mediated by APO–1(Fas/CD95)", Abstract, Nature 373:438, 1995.
Vossbeck et al., "Direct transforming activity of TGF–beta on rat fibroblasts", Abstract, Int. J. Cancer 61:92, 1995.
Goruppi et al., "Dissection of c–myc domains involved in S phase induction of NIH3T3 fibroblasts", Abstract, Oncogene 9:1537, 1994.
Fernandez et al., "Differential sensitivity of normal and Ha–ras–transformed C3H mouse embryo fibroblasts to tumor necrosis factor: . . . ", Abstract, Oncogene 9:2009, 1994.
Harrington et al., "c–Myc–induced apoptosis in fibroblasts is inherited by specific cytokines", Abstract, EMBO J. 13:3286, 1994.
Itoh et al., "A novel protein required for apoptosis . . . ", Abstract, J. Biol. Chem. 268:10932, 1993.
Melino et al., "Tissue transglutaminase and apoptosis: sense and antisense transfection studies . . . " Abstract, Mol. Cell. Biol. 14:6584, 1994.

(List continued on next page.)

*Primary Examiner*—Frank C. Eisenschenk
*Assistant Examiner*—Patrick J. Nolan
*Attorney, Agent, or Firm*—Clark & Elbing LLP; Kristina Bieker-Brady

[57] ABSTRACT

Disclosed is substantially pure DNA encoding mammalian IAP polypeptides; substantially pure polypeptides; and methods of using such DNA to express the IAP polypeptides in cells and animals to inhibit apoptosis. Also disclosed are conserved regions characteristic of the IAP family and primers and probes for the identification and isolation of additional IAP genes. In addition, methods for treating diseases and disorders involving apoptosis are provided.

26 Claims, 25 Drawing Sheets

OTHER PUBLICATIONS

Rosenbaum et al., "Evidence for hypoxia–induced, programmed cell death of cultured neurons", Abstract, Ann. Neurol. 36:864, 1994.

Sato et al., "Neuronal differentiation of PC12 cells as a result of prevention of cell death by bcl–2", Abstract, J. Neurobiol. 25:1227, 1994.

Ferrari et al. "N–acetylcysteine (D–and L–stereoisomers) prevents apoptotic death of neuronal cells", Abstract, J. Neurosci. 1516:2857, 1995.

Talley et al., "Tumor: necrosis factor alpha–induced apoptosis in human neuronal cells . . . ", Abstract, Mol. Cell. Biol. 1585:2359, 1995.

Rabizadeh et al., "Expression of the baculovirus p35 gene inhibits mammalian neural cell death", Abstract, J. Neurochem. 61:2318, 1993.

Birnbaum et al., "An apoptosis–inhibiting gene from a nuclear polyhedrosis virus encoding a polypeptide with Cys/His sequence motifs", Abstract, J. Virol. 68:2521, 1994.

Liston et al., "Suppression of apoptosis in mammalian cells by NAIP and a related family of IAP genes", *Nature,* 379: 349–353, (1996).

Duckett et al., "A conserved family of cellular genes related to the baculovirus iap gene and encoding apoptosis inhibitors", *The EMBO Journal,* 15: 2685–2694, (1996).

Clem et al., "Anti–apoptotic gene baculovirus", *Cell Death and Differentiation,* 3: 9–16, (1996).

Rothe et al., "The TNFR2–TRAF Signaling Complex Contains Two Novel Proteins Related to Baculoviral Inhibitor of Apoptosis Proteins", *Cell,* 83: 1243–1252, (1995).

Johnstone et al. Immunochemistry in Practice 2nd Edition. Blackwell Scientific Publications London 1987.

Campbell, Alisa Monoclonal Antibody Technology, Elsevier Science Publishers B.V. New York, New York 1984.

HUMAN xiap

```
        gaaaaggtggacaagtcctaatttcaagagaagatgacttttaacagttttgaaggatct
     1  ------------------------------------------------------------+  60
a                                     M  T  F  N  S  F  E  G  S    - aaaacttgtgtacctgcagacatcaataaggaagaagaatttgtagaagagtttaataga
    61  ------------------------------------------------------------+ 120
a       K  T  C  V  P  A  D  I  N  K  E  E  E  F  V  E  E  F  N  R   - ttaaaaacttttgctaattttccaagtggtagtcctgtttcagcatcaacactggcacga
   121  ------------------------------------------------------------+ 180
a       L  K  T  F  A  N  F  P  S  G  S  P  V  S  A  S  T  L  A  R   - gcagggtttctttatactggtgaaggagataccgtgcggtgctttagttgtcatgcagct
   181  ------------------------------------------------------------+ 240
a       A  G  F  L  Y  T  G  E  G  D  T  V  R  C  F  S  C  H  A  A   - gtagatagatggcaatatggagactcagcagttggaagacacaggaaagtatccccaaat
   241  ------------------------------------------------------------+ 300
a       V  D  R  W  Q  Y  G  D  S  A  V  G  R  H  R  K  V  S  P  N   - tgcagatttatcaacggcttttatcttgaaaatagtgccacgcagtctacaaattctggt
   301  ------------------------------------------------------------+ 360
a       C  R  F  I  N  G  F  Y  L  E  N  S  A  T  Q  S  T  N  S  G   - atccagaatggtcagtacaaagttgaaaactatctgggaagcagagatcattttgcctta
   361  ------------------------------------------------------------+ 420
a       I  Q  N  G  Q  Y  K  V  E  N  Y  L  G  S  R  D  H  F  A  L   - gacaggccatctgagacacatgcagactatcttttgagaactgggcaggttgtagatata
   421  ------------------------------------------------------------+ 480
a       D  R  P  S  E  T  H  A  D  Y  L  L  R  T  G  Q  V  V  D  I   - tcagacaccatatacccgaggaaccctgccatgtattgtgaagaagctagattaaagtcc
   481  ------------------------------------------------------------+ 540
a       S  D  T  I  Y  P  R  N  P  A  M  Y  C  E  E  A  R  L  K  S   - tttcagaactggccagactatgctcacctaaccccaagagagttagcaagtgctggactc
   541  ------------------------------------------------------------+ 600
a       F  Q  N  W  P  D  Y  A  H  L  T  P  R  E  L  A  S  A  G  L   -
```

Fig. 1 (pg. 1 of 4)

HUMAN xiap

```
       tactacacaggtattggtgaccaagtgcagtgcttttgttgtggtggaaaactgaaaaat
  601  ------------------------------------------------------------  660
        Y  Y  T  G  I  G  D  Q  V  Q  C  F  C  C  G  G  K  L  K  N   -
a      tgggaaccttgtgatcgtgcctggtcagaacacaggcgacactttcctaattgcttcttt
  661  ------------------------------------------------------------  720
        W  E  P  C  D  R  A  W  S  E  H  R  R  H  F  P  N  C  F  F   -
a      gtttttgggccggaatcttaatattcgaagtgaatctgatgctgtgagttctgataggaat
  721  ------------------------------------------------------------  780
        V  L  G  R  N  L  N  I  R  S  E  S  D  A  V  S  S  D  R  N   -
a      ttcccaaattcaacaaatcttccaagaaatccatccatggcagattatgaagcacggatc
  781  ------------------------------------------------------------  840
        F  P  N  S  T  N  L  P  R  N  P  S  M  A  D  Y  E  A  R  I   -
a      tttacttttgggacatggatatactcagttaacaaggagcagcttgcaagagctggattt
  841  ------------------------------------------------------------  900
        F  T  F  G  T  W  I  Y  S  V  N  K  E  Q  L  A  R  A  G  F   -
a      tatgctttaggtgaaggtgataaagtaaagtgctttcactgtggaggagggctaactgat
  901  ------------------------------------------------------------  960
        Y  A  L  G  E  G  D  K  V  K  C  F  H  C  G  G  L  T  D   -
a      tggaagcccagtgaagacccttgggaacaacatgctaaatggtatccagggtgcaaatat
  961  ------------------------------------------------------------  1020
        W  K  P  S  E  D  P  W  E  Q  H  A  K  W  Y  P  G  C  K  Y   -
a      ctgttagaacagaagggacaagaatatataaacaatattcatttaactcattcacttgag
 1021  ------------------------------------------------------------  1080
        L  L  E  Q  K  G  Q  E  Y  I  N  N  I  H  L  T  H  S  L  E   -
a      gagtgtctggtaagaactactgagaaaacaccatcactaactagaagaattgatgatacc
 1081  ------------------------------------------------------------  1140
        E  C  L  V  R  T  T  E  K  T  P  S  L  T  R  R  I  D  D  T   -
a      atcttccaaaatcctatggtacaagaagctatacgaatgggggttcagtttcaaggacatt
 1141  ------------------------------------------------------------  1200
        I  F  Q  N  P  M  V  Q  E  A  I  R  M  G  F  S  F  K  D  I   -
a      aagaaaataatggaggaaaaaattcagatatctgggagcaactataaatcacttgaggtt
 1201  ------------------------------------------------------------  1260
        K  K  I  M  E  E  K  I  Q  I  S  G  S  N  Y  K  S  L  E  V   -
a      ctggttgcagatctagtgaatgctcagaaagacagtatgcaagatgagtcaagtcagact
 1261  ------------------------------------------------------------  1320
        L  V  A  D  L  V  N  A  Q  K  D  S  M  Q  D  E  S  S  Q  T   -
a      tcattacagaaagagattagtactgaagagcagctaaggcgcctgcaagaggagaagctt
 1321  ------------------------------------------------------------  1380
a       S  L  Q  K  E  I  S  T  E  E  Q  L  R  R  L  Q  E  E  K  L   -
```

Fig. 1 (pg. 2 of 4)

HUMAN xiap

```
     tgcaaaatctgtatggatagaaatattgctatcgttttttgttccttgtggacatctagtc
1381 ------------+---------+---------+---------+---------+---------+ 1440
 a    C  K  I  C  M  D  R  N  I  A  I  V  F  V  P  C  G  H  L  V   - acttgtaaacaatgtgctgaagcagttgacaagtgtcccatgtgctacacagtcattact
1441 ------------+---------+---------+---------+---------+---------+ 1500
 a    T  C  K  Q  C  A  E  A  V  D  K  C  P  M  C  Y  T  V  I  T   - ttcaagcaaaaaattttttatgtcttaatctaactctatagtaggcatgttatgttgttct
1501 ------------+---------+---------+---------+---------+---------+ 1560
 a    F  K  Q  K  I  F  M  S  *                                    - tattaccctgattgaatgtgtgatgtgaactgactttaagtaatcaggattgaattccat
1561 ------------+---------+---------+---------+---------+---------+ 1620
 a                                                                  - tagcatttgctaccaagtaggaaaaaaaatgtacatggcagtgttttagttggcaatata
1621 ------------+---------+---------+---------+---------+---------+ 1680
 a                                                                  - atctttgaatttcttgattttttcagggtattagctgtattatccattttttttactgtta
1681 ------------+---------+---------+---------+---------+---------+ 1740
 a                                                                  - tttaattgaaaccatagactaagaataagaagcatcatactataactgaacacaatgtgt
1741 ------------+---------+---------+---------+---------+---------+ 1800
 a                                                                  - attcatagtatactgatttaatttctaagtgtaagtgaattaatcatctggattttttat
1801 ------------+---------+---------+---------+---------+---------+ 1860
 a                                                                  - tcttttcagataggcttaacaaatggagctttctgtatataaatgtggagattagagtta
1861 ------------+---------+---------+---------+---------+---------+ 1920
 a                                                                  - atctccccaatcacataatttgttttgtgtgaaaaaggaataaattgttccatgctggtg
1921 ------------+---------+---------+---------+---------+---------+ 1980
 a                                                                  - gaaagatagagattgttttagaggttggttgttgtgttttaggattctgtccatttttct
1981 ------------+---------+---------+---------+---------+---------+ 2040
 a                                                                  - tgtaaagnnataaacacgnacntgtgcgaaatatntttgtaaagtgatttgccattnttg
2041 ------------+---------+---------+---------+---------+---------+ 2100
 a                                                                  -
```

Fig. 1 (pg. 3 of 4)

HUMAN xiap

```
      aaagcgtatttaatgatagaatactatcgagccaacatgtactgacatggaaagatgtca
2101  ---------+---------+---------+---------+---------+---------+ 2160
a                                                                 - nagatatgttaagtgtaaaatgcaagtggcnnnacactatgtatagtctgagccagatca
2161  ---------+---------+---------+---------+---------+---------+ 2220
a                                                                 - aagtatgtatgttnttaatatgcatagaacnanagatttggaaagatatacaccaaactg
2221  ---------+---------+---------+---------+---------+---------+ 2280
a                                                                 - ttaaatgtggtttctcttcggggagggggggattgggggagggggccccagagggggttttta
2281  ---------+---------+---------+---------+---------+---------+ 2340
a                                                                 - naggggccttttcactttcnactttttttcattttgttctgttcgnattttttataagtat
2341  ---------+---------+---------+---------+---------+---------+ 2400
a                                                                 - gtanaccccnaagggttttatggnaactaacatcagtaacctaaccccccgtgactatcct
2401  ---------+---------+---------+---------+---------+---------+ 2460
a                                                                 - gtnctcttcctagggagctgtnttgtttcccacccaccacccttccctctgaacaaatgc
2461  ---------+---------+---------+---------+---------+---------+ 2520
a                                                                 - ctgagtgctggggcactttn
2521  ---------+---------+ 2540
a                        -
```

Fig. 1 (pg. 4 of 4)

HUMAN hiap 1

```
    TCCTTGAGATGTATCAGTATAGGATTTAGGATCTCCATGTTGGAACTCTAAATGCATAGA
  1 ---------+---------+---------+---------+---------+---------+ 60
c                                                                -

AATGGAAATAATGGAAATTTTTCATTTTGGCTTTTCAGCCTAGTATTAAAACTGATAAAA
 61 ---------+---------+---------+---------+---------+---------+ 120
c                                                                -

GCAAAGCCATGCACAAAACTACCTCCCTAGAGAAAGGCTAGTCCCTTTTCTTCCCCATTC
121 ---------+---------+---------+---------+---------+---------+ 180
c                                                                -

ATTTCATTATGAACATAGTAGAAAACAGCATATTCTTATCAAATTTGATGAAAAGCGCCA
181 ---------+---------+---------+---------+---------+---------+ 240
c            M  N  I  V  E  N  S  I  F  L  S  N  L  M  K  S  A  N -

ACACGTTTGAACTGAAATACGACTTGTCATGTGAACTGTACCGAATGTCTACGTATTCCA
241 ---------+---------+---------+---------+---------+---------+ 300
c    T  F  E  L  K  Y  D  L  S  C  E  L  Y  R  M  S  T  Y  S  T -

CTTTTCCTGCTGGGGTTCCTGTCTCAGAAAGGAGTCTTGCTCGTGCTGGTTTCTATTACA
301 ---------+---------+---------+---------+---------+---------+ 360
c    F  P  A  G  V  P  V  S  E  R  S  L  A  R  A  G  F  Y  Y  T -

CTGGTGTGAATGACAAGGTCAAATGCTTCTGTTGTGGCCTGATGCTGGATAACTGGAAAA
361 ---------+---------+---------+---------+---------+---------+ 420
c    G  V  N  D  K  V  K  C  F  C  C  G  L  M  L  D  N  W  K  R -

GAGGAGACAGTCCTACTGAAAAGCATAAAAAGTTGTATCCTAGCTGCAGATTCGTTCAGA
421 ---------+---------+---------+---------+---------+---------+ 480
c    G  D  S  P  T  E  K  H  K  K  L  Y  P  S  C  R  F  V  Q  S -

GTCTAAATTCCGTTAACAACTTGGAAGCTACCTCTCAGCCTACTTTTCCTTCTTCAGTAA
481 ---------+---------+---------+---------+---------+---------+ 540
c    L  N  S  V  N  N  L  E  A  T  S  Q  P  T  F  P  S  S  V  T -

CACATTCCACACACTCATTACTTCCGGGTACAGAAAACAGTGGATATTCCGTGGCTCTT
541 ---------+---------+---------+---------+---------+---------+ 600
c    H  S  T  H  S  L  L  P  G  T  E  N  S  G  Y  F  R  G  S  Y -

ATTCAAACTCTCCATCAAATCCTGTAAACTCCAGAGCAAATCAAGAATTTTCTGCCTTGA
601 ---------+---------+---------+---------+---------+---------+ 660
c    S  N  S  P  S  N  P  V  N  S  R  A  N  Q  E  F  S  A  L  M -
```

Fig. 2 (pg. 1 of 4)

HUMAN hiap 1

```
      TGAGAAGTTCCTACCCCTGTCCAATGAATAACGAAAATGCCAGATTACTTACTTTTCAGA
  661 ---------+---------+---------+---------+---------+---------+ 720
c       R  S  S  Y  P  C  P  M  N  N  E  N  A  R  L  L  T  F  Q  T  -

CATGGCCATTGACTTTTCTGTCGCCAACAGATCTGGCACGAGCAGGCTTTTACTACATAG
  721 ---------+---------+---------+---------+---------+---------+ 780
c       W  P  L  T  F  L  S  P  T  D  L  A  R  A  G  F  Y  Y  I  G  -

GACCTGGAGACAGAGTGGCTTGCTTTGCCTGTGGTGGAAAATTGAGCAATTGGGAACCGA
  781 ---------+---------+---------+---------+---------+---------+ 840
c       P  G  D  R  V  A  C  F  A  C  G  G  K  L  S  N  W  E  P  K  -

AGGATAATGCTATGTCAGAACACCTGAGACATTTTCCCAAATGCCCATTTATAGAAAATC
  841 ---------+---------+---------+---------+---------+---------+ 900
c       D  N  A  M  S  E  H  L  R  H  F  P  K  C  P  F  I  E  N  Q  -

AGCTTCAAGACACTTCAAGATACACAGTTTCTAATCTGAGCATGCAGACACATGCAGCCC
  901 ---------+---------+---------+---------+---------+---------+ 960
c       L  Q  D  T  S  R  Y  T  V  S  N  L  S  M  Q  T  H  A  A  R  -

GCTTTAAAACATTCTTTAACTGGCCCTCTAGTGTTCTAGTTAATCCTGAGCAGCTTGCAA
  961 ---------+---------+---------+---------+---------+---------+ 1020
c       F  K  T  F  F  N  W  P  S  S  V  L  V  N  P  E  Q  L  A  S  -

GTGCGGGTTTTTATTATGTGGGTAACAGTGATGATGTCAAATGCTTTTGCTGTGATGGTG
 1021 ---------+---------+---------+---------+---------+---------+ 1080
c       A  G  F  Y  Y  V  G  N  S  D  D  V  K  C  F  C  C  D  G  G  -

GACTCAGGTGTTGGGAATCTGGAGATGATCCATGGGTTCAACATGCCAAGTGGTTTCCAA
 1081 ---------+---------+---------+---------+---------+---------+ 1140
c       L  R  C  W  E  S  G  D  D  P  W  V  Q  H  A  K  W  F  P  R  -

GGTGTGAGTACTTGATAAGAATTAAAGGACAGGAGTTCATCCGTCAAGTTCAAGCCAGTT
 1141 ---------+---------+---------+---------+---------+---------+ 1200
c       C  E  Y  L  I  R  I  K  G  Q  E  F  I  R  Q  V  Q  A  S  Y  -

ACCCTCATCTACTTGAACAGCTGCTATCCACATCAGACAGCCCAGGAGATGAAAATGCAG
 1201 ---------+---------+---------+---------+---------+---------+ 1260
c       P  H  L  L  E  Q  L  L  S  T  S  D  S  P  G  D  E  N  A  E  -

AGTCATCAATTATCCATTTGGAACCTGGAGAAGACCATTCAGAAGATGCAATCATGATGA
 1261 ---------+---------+---------+---------+---------+---------+ 1320
c       S  S  I  I  H  L  E  P  G  E  D  H  S  E  D  A  I  M  M  N  -

ATACTCCTGTGATTAATGCTGCCGTGGAAATGGGCTTTAGTAGAAGCCTGGTAAAACAGA
 1321 ---------+---------+---------+---------+---------+---------+ 1380
c       T  P  V  I  N  A  A  V  E  M  G  F  S  R  S  L  V  K  Q  T  -
```

Fig. 2 (pg. 2 of 4)

HUMAN hiap 1

```
      CAGTTCAGAGAAAAATCCTAGCAACTGGAGAGAATTATAGACTAGTCAATGATCTTGTGT
1381  ------------------------------------------------------------  1440
c      V  Q  R  K  I  L  A  T  G  E  N  Y  R  L  V  N  D  L  V  L  -

TAGACTTACTCAATGCAGAAGATGAAATAAGGGAAGAGGAGAGAGAAAGAGCAACTGAGG
1441  ------------------------------------------------------------  1500
c      D  L  L  N  A  E  D  E  I  R  E  E  E  R  A  T  E  E  -

AAAAAGAATCAAATGATTTATTATTAATCCGGAAGAATAGAATGGCACTTTTTCAACATT
1501  ------------------------------------------------------------  1560
c      K  E  S  N  D  L  L  I  R  K  N  R  M  A  L  F  Q  H  L  -

TGACTTGTGTAATTCCAATCCTGGATAGTCTACTAACTGCCGGAATTATTAATGAACAAG
1561  ------------------------------------------------------------  1620
c      T  C  V  I  P  I  L  D  S  L  L  T  A  G  I  I  N  E  Q  E  -

AACATGATGTTATTAAACAGAAGACACAGACGTCTTTACAAGCAAGAGAACTGATTGATA
1621  ------------------------------------------------------------  1680
c      H  D  V  I  K  Q  K  T  Q  T  S  L  Q  A  R  E  L  I  D  T  -

CGATTTTAGTAAAAGGAAATATTGCAGCCACTGTATTCAGAAACTCTCTGCAAGAAGCTG
1681  ------------------------------------------------------------  1740
c      I  L  V  K  G  N  I  A  A  T  V  F  R  N  S  L  Q  E  A  E  -

AAGCTGTGTTATATGAGCATTTATTTGTGCAACAGGACATAAAATATATTCCCACAGAAG
1741  ------------------------------------------------------------  1800
c      A  V  L  Y  E  H  L  F  V  Q  Q  D  I  K  Y  I  P  T  E  D  -

ATGTTTCAGATCTACCAGTGGAAGAACAATTGCGGAGACTACCAGAAGAAAGAACATGTA
1801  ------------------------------------------------------------  1860
c      V  S  D  L  P  V  E  E  Q  L  R  R  L  P  E  E  R  T  C  K  -

AAGTGTGTATGGACAAAGAAGTGTCCATAGTGTTTATTCCTTGTGGTCATCTAGTAGTAT
1861  ------------------------------------------------------------  1920
c      V  C  M  D  K  E  V  S  I  V  F  I  P  C  G  H  L  V  V  C  -

GCAAAGATTGTGCTCCTTCTTTAAGAAAGTGTCCTATTTGTAGGAGTACAATCAAGGGTA
1921  ------------------------------------------------------------  1980
c      K  D  C  A  P  S  L  R  K  C  P  I  C  R  S  T  I  K  G  T  -

CAGTTCGTACATTTCTTTCATGAAGAAGAACCAAAACATCGTCTAAACTTTAGAATTAAT
1981  ------------------------------------------------------------  2040
c      V  R  T  F  L  S  *                                        -

TTATTAAATGTATTATAACTTTAACTTTTATCCTAATTTGGTTTCCTTAAAATTTTTATT
2041  ------------------------------------------------------------  2100
c                                                                 -
```

Fig. 2 (pg. 3 of 4)

HUMAN hiap 1

```
     TATTTACAACTCAAAAAACATTGTTTTGTGTAACATATTTATATATGTATCTAAACCATA
2101 ---------+---------+---------+---------+---------+---------+ 2160
c                                                                -

TGAACATATATTTTTTAGAAACTAAGAGAATGATAGGCTTTTGTTCTTATGAACGAAAAA
2161 ---------+---------+---------+---------+---------+---------+ 2220
c                                                                -

GAGGTAGCACTACAAACACAATATTCAATCCAAATTTCAGCATTATTGAAATTGTAAGTG
2221 ---------+---------+---------+---------+---------+---------+ 2280
c                                                                -

AAGTAAAACTTAAGATATTTGAGTTAACCTTTAAGAATTTTAAATATTTTGGCATTGTAC
2281 ---------+---------+---------+---------+---------+---------+ 2340
c                                                                -

TAATACCGGGAACATGAAGCCAGGTGTGGTGGTATGTACCTGTAGTCCCAGGCTGAGGCA
2341 ---------+---------+---------+---------+---------+---------+ 2400
c                                                                -

AGAGAATTACTTGAGCCCAGGAGTTTGAATCCATCCTGGGCAGCATACTGAGACCCTGCC
2401 ---------+---------+---------+---------+---------+---------+ 2460
c                                                                -

TTTAAAAACXAACAGXACCAAAXCCAAACACCAGGGACACATTTCTCTGTCTTTTTTGAT
2461 ---------+---------+---------+---------+---------+---------+ 2520
c                                                                -

CAGTGTCCTATACATCGAAGGTGTGCATATATGTTGAATCACATTTTAGGGACATGGTGT
2521 ---------+---------+---------+---------+---------+---------+ 2580
c                                                                -

TTTTATAAAGAATTCTGTGAGXAAAAATTTAATAAAGCAACCXAAATTACTCTTAAAAAA
2581 ---------+---------+---------+---------+---------+---------+ 2640
c                                                                -

AAAAAAAAAAAAAAAAACTCGAGGGGCCCGTACCAAT
2641 ---------+---------+---------+------  2676
c                                         -
```

Fig. 2 (pg. 4 of 4)

HUMAN hiap 2

```
        TTAGGTTACCTGAAAGAGTTACTACAACCCCAAAGAGTTGTGTTCTAAGTAGTATCTTGG
     1  ------------+---------+---------+---------+---------+---------+  60
  a                                                                      -

TAATTCAGAGAGATACTCATCCTACCTGAATATAAACTGAGATAAATCCAGTAAAGAAAG
    61  ------------+---------+---------+---------+---------+---------+ 120
  a                                                                      -

TGTAGTAAATTCTACATAAGAGTCTATCATTGATTTCTTTTTGTGGTGGAAATCTTAGTT
   121  ------------+---------+---------+---------+---------+---------+ 180
  a                                                                      -

CATGTGAAGAAATTTCATGTGAATGTTTTAGCTATCAAACAGTACTGTCACCTACTCATG
   181  ------------+---------+---------+---------+---------+---------+ 240
  a                                                                 M    -

CACAAAACTGCCTCCCAAAGACTTTTCCCAGGTCCCTCGTATCAAAACATTAAGAGTATA
   241  ------------+---------+---------+---------+---------+---------+ 300
  a      H  K  T  A  S  Q  R  L  F  P  G  P  S  Y  Q  N  I  K  S  I     -

ATGGAAGATAGCACGATCTTGTCAGATTGGACAAACAGCAACAAACAAAAAATGAAGTAT
   301  ------------+---------+---------+---------+---------+---------+ 360
  a      M  E  D  S  T  I  L  S  D  W  T  N  S  N  K  Q  K  M  K  Y     -

GACTTTTCCTGTGAACTCTACAGAATGTCTACATATTCAACTTTCCCCGCCGGGGTGCCT
   361  ------------+---------+---------+---------+---------+---------+ 420
  a      D  F  S  C  E  L  Y  R  M  S  T  Y  S  T  F  P  A  G  V  P     -

GTCTCAGAAAGGAGTCTTGCTCGTGCTGGTTTTTATTATACTGGTGTGAATGACAAGGTC
   421  ------------+---------+---------+---------+---------+---------+ 480
  a      V  S  E  R  S  L  A  R  A  G  F  Y  Y  T  G  V  N  D  K  V     -

AAATGCTTCTGTTGTGGCCTGATGCTGGATAACTGGAAACTAGGAGACAGTCCTATTCAA
   481  ------------+---------+---------+---------+---------+---------+ 540
  a      K  C  F  C  C  G  L  M  L  D  N  W  K  L  G  D  S  P  I  Q     -

AAGCATAAACAGCTATATCCTAGCTGTAGCTTTATTCAGAATCTGGTTTCAGCTAGTCTG
   541  ------------+---------+---------+---------+---------+---------+ 600
  a      K  H  K  Q  L  Y  P  S  C  S  F  I  Q  N  L  V  S  A  S  L     -
```

Fig. 3 (pg. 1 of 4)

HUMAN hiap 2

```
      GGATCCACCTCTAAGAATACGTCTCCAATGAGAAACAGTTTTGCACATTCATTATCTCCC
  601 ------------+---------+---------+---------+---------+---------+ 660
a      G  S  T  S  K  N  T  S  P  M  R  N  S  F  A  H  S  L  S  P   -

ACCTTGGAACATAGTAGCTTGTTCAGTGGTTCTTACTCCAGCCTTCCTCCAAACCCTCTT
  661 ------------+---------+---------+---------+---------+---------+ 720
a      T  L  E  H  S  S  L  F  S  G  S  Y  S  S  L  P  P  N  P  L   -

AATTCTAGAGCAGTTGAAGACATCTCTTCATCGAGGACTAACCCCTACAGTTATGCAATG
  721 ------------+---------+---------+---------+---------+---------+ 780
a      N  S  R  A  V  E  D  I  S  S  S  R  T  N  P  Y  S  Y  A  M   -

AGTACTGAAGAAGCCAGATTTCTTACCTACCATATGTGGCCATTAACTTTTTTGTCACCA
  781 ------------+---------+---------+---------+---------+---------+ 840
a      S  T  E  E  A  R  F  L  T  Y  H  M  W  P  L  T  F  L  S  P   -

TCAGAATTGGCAAGAGCTGGTTTTTATTATATAGGACCTGGAGATAGGGTAGCCTGCTTT
  841 ------------+---------+---------+---------+---------+---------+ 900
a      S  E  L  A  R  A  G  F  Y  Y  I  G  P  G  D  R  V  A  C  F   -

GCCTGTGGTGGGAAGCTCAGTAACTGGGAACCAAAGGATGATGCTATGTCAGAACACCGG
  901 ------------+---------+---------+---------+---------+---------+ 960
a      A  C  G  G  K  L  S  N  W  E  P  K  D  D  A  M  S  E  H  R   -

AGGCATTTTCCCAACTGTCCATTTTTGGAAAATTCTCTAGAAACTCTGAGGTTTAGCATT
  961 ------------+---------+---------+---------+---------+---------+ 1020
a      R  H  F  P  N  C  P  F  L  E  N  S  L  E  T  L  R  F  S  I   -

TCAAATCTGAGCATGCAGACACATGCAGCTCGAATGAGAACATTTATGTACTGGCCATCT
 1021 ------------+---------+---------+---------+---------+---------+ 1080
a      S  N  L  S  M  Q  T  H  A  A  R  M  R  T  F  M  Y  W  P  S   -

AGTGTTCCAGTTCAGCCTGAGCAGCTTGCAAGTGCTGGTTTTTATTATGTGGGTCGCAAT
 1081 ------------+---------+---------+---------+---------+---------+ 1140
a      S  V  P  V  Q  P  E  Q  L  A  S  A  G  F  Y  Y  V  G  R  N   -

GATGATGTCAAATGCTTTGGTTGTGATGGTGGCTTGAGGTGTTGGGAATCTGGAGATGAT
 1141 ------------+---------+---------+---------+---------+---------+ 1200
a      D  D  V  K  C  F  G  C  D  G  G  L  R  C  W  E  S  G  D  D   -

CCATGGGTAGAACATGCCAAGTGGTTTCCAAGGTGTGAGTTCTTGATACGAATGAAAGGC
 1201 ------------+---------+---------+---------+---------+---------+ 1260
a      P  W  V  E  H  A  K  W  F  P  R  C  E  F  L  I  R  M  K  G   -

CAAGAGTTTGTTGATGAGATTCAAGGTAGATATCCTCATCTTCTTGAACAGCTGTTGTCA
 1261 ------------+---------+---------+---------+---------+---------+ 1320
a      Q  E  F  V  D  E  I  Q  G  R  Y  P  H  L  L  E  Q  L  L  S   -
```

Fig. 3 (pg. 2 of 4)

HUMAN hiap 2

```
      ACTTCAGATACCACTGGAGAAGAAAATGCTGACCCACCAATTATTCATTTTGGACCTGGA
1321  ------------------------------------------------------------  1380
a      T  S  D  T  T  G  E  E  N  A  D  P  P  I  I  H  F  G  P  G   -

GAAAGTTCTTCAGAAGATGCTGTCATGATGAATACACCTGTGGTTAAATCTGCCTTGGAA
1381  ------------------------------------------------------------  1440
a      E  S  S  E  D  A  V  M  M  N  T  P  V  V  K  S  A  L  E   -

ATGGGCTTTAATAGAGACCTGGTGAAACAAACAGTTCTAAGTAAAATCCTGACAACTGGA
1441  ------------------------------------------------------------  1500
a      M  G  F  N  R  D  L  V  K  Q  T  V  L  S  K  I  L  T  T  G   -

GAGAACTATAAAACAGTTAATGATATTGTGTCAGCACTTCTTAATGCTGAAGATGAAAAA
1501  ------------------------------------------------------------  1560
a      E  N  Y  K  T  V  N  D  I  V  S  A  L  L  N  A  E  D  E  K   -

AGAGAAGAGGAGAAGGAAAAACAAGCTGAAGAAATGGCATCAGATGATTTGTCATTAATT
1561  ------------------------------------------------------------  1620
a      R  E  E  E  K  E  K  Q  A  E  E  M  A  S  D  D  L  S  L  I   -

CGGAAGAACAGAATGGCTCTCTTTCAACAATTGACATGTGTGCTTCCTATCCTGGATAAT
1621  ------------------------------------------------------------  1680
a      R  K  N  R  M  A  L  F  Q  Q  L  T  C  V  L  P  I  L  D  N   -

CTTTTAAAGGCCAATGTAATTAATAAACAGGAACATGATATTATTAAACAAAAAACACAG
1681  ------------------------------------------------------------  1740
a      L  L  K  A  N  V  I  N  K  Q  E  H  D  I  I  K  Q  K  T  Q   -

ATACCTTTACAAGCGAGAGAACTGATTGATACCATTTGGGTTAAAGGAAATGCTGCGGCC
1741  ------------------------------------------------------------  1800
a      I  P  L  Q  A  R  E  L  I  D  T  I  W  V  K  G  N  A  A  A   -

AACATCTTCAAAAACTGTCTAAAAGAAATTGACTCTACATTGTATAAGAACTTATTTGTG
1801  ------------------------------------------------------------  1860
a      N  I  F  K  N  C  L  K  E  I  D  S  T  L  Y  K  N  L  F  V   -

GATAAGAATATGAAGTATATTCCAACAGAAGATGTTTCAGGTCTGTCACTGGAAGAACAA
1861  ------------------------------------------------------------  1920
a      D  K  N  M  K  Y  I  P  T  E  D  V  S  G  L  S  L  E  E  Q   -

TTGAGGAGGTTGCAAGAAGAACGAACTTGTAAAGTGTGTATGGACAAAGAAGTTTCTGTT
1921  ------------------------------------------------------------  1980
a      L  R  R  L  Q  E  E  R  T  C  K  V  C  M  D  K  E  V  S  V   -

GTATTTATTCCTTGTGGTCATCTGGTAGTATGCCAGGAATGTGCCCCTTCTCTAAGAAAA
1981  ------------------------------------------------------------  2040
a      V  F  I  P  C  G  H  L  V  V  C  Q  E  C  A  P  S  L  R  K   -
```

Fig. 3 (pg. 3 of 4)

HUMAN hiap 2

```
     TGCCCTATTTGCAGGGGTATAATCAAGGGTACTGTTCGTACATTTCTCTCTTAAAGAAAA
2041 ------------------------------------------------------------+ 2100
a     C  P  I  C  R  G  I  I  K  G  T  V  R  T  F  L  S  *       -

ATAGTCTATATTTTAACCTGCATAAAAAGGTCTTTAAAATATTGTTGAACACTTGAAGCC
2101 ------------------------------------------------------------+ 2160
a                                                                -

ATCTAAAGTAAAAAGGGAATTATGAGTTTTTCAATTAGTAACATTCATGTTCTAGTCTGC
2161 ------------------------------------------------------------+ 2220
a                                                                -

TTTGGTACTAATAATCTTGTTTCTGAAAAGATGGTATCATATATTTAATCTTAATCTGTT
2221 ------------------------------------------------------------+ 2280
a                                                                -

TATTTACAAGGGAAGATTTATGTTTGGTGAACTATATTAGTATGTATGTGTACCTAAGGG
2281 ------------------------------------------------------------+ 2340
a                                                                -

AGTAGCGTCXCTGCTTGTTATGCATCATTTCAGGAGTTACTGGATTTGTTGTTCTTTCAG
2341 ------------------------------------------------------------+ 2400
a                                                                -

AAAGCTTTGAAXACTAAATTATAGTGTAGAAAAGAACTGGAAACCAGGAACTCTGGAGTT
2401 ------------------------------------------------------------+ 2460
a                                                                -

CATCAGAGTTATGGTGCCGAATTGTCTTTGGTGCTTTTCACTTGTGTTTTAAAATAAGGA
2461 ------------------------------------------------------------+ 2520
a                                                                -

TTTTTCTCTTATTTCTCCCCCTAGTTTGTGAGAAACATCTCAATAAAGTGCTTTAAAAAG
2521 ------------------------------------------------------------+ 2580
a                                                                -
```

Fig. 3 (pg. 4 of 4)

MOUSE xiap

```
      GACACTCTGCTGGGCGGCGGGCCGCCCTCCTCCGGGACCTCCCCTCGGGAACCGTCGCCC
  1   ---------+---------+---------+---------+---------+---------+ 60
a                                                                 -

GCGGCGCTTAGTTAGGACTGGAGTGCTTGGCGCGAAAAGGTGGACAAGTCCTATTTTCCA
 61   ---------+---------+---------+---------+---------+---------+ 120
a                                                                 -

GAGAAGATGACTTTTAACAGTTTTGAAGGAACTAGAACTTTTGTACTTGCAGACACCAAT
121   ---------+---------+---------+---------+---------+---------+ 180
a           M  T  F  N  S  F  E  G  T  R  T  F  V  L  A  D  T  N -

AAGGATGAAGAATTTGTAGAAGAGTTTAATAGATTAAAAACATTTGCTAACTTCCCAAGT
181   ---------+---------+---------+---------+---------+---------+ 240
a      K  D  E  E  F  V  E  E  F  N  R  L  K  T  F  A  N  F  P  S -

AGTAGTCCTGTTTCAGCATCAACATTGGCGCGAGCTGGGTTTCTTTATACCGGTGAAGGA
241   ---------+---------+---------+---------+---------+---------+ 300
a      S  S  P  V  S  A  S  T  L  A  R  A  G  F  L  Y  T  G  E  G -

GACACCGTGCAATGTTTCAGTTGTCATGCGGCAATAGATAGATGGCAGTATGGAGACTCA
301   ---------+---------+---------+---------+---------+---------+ 360
a      D  T  V  Q  C  F  S  C  H  A  A  I  D  R  W  Q  Y  G  D  S -

GCTGTTGGAAGACACAGGAGAATATCCCCAAATTGCAGATTTATCAATGGTTTTTATTTT
361   ---------+---------+---------+---------+---------+---------+ 420
a      A  V  G  R  H  R  R  I  S  P  N  C  R  F  I  N  G  F  Y  F -

GAAAATGGTGCTGCACAGTCTACAAATCCTGGTATCCAAAATGGCCAGTACAAATCTGAA
421   ---------+---------+---------+---------+---------+---------+ 480
a      E  N  G  A  A  Q  S  T  N  P  G  I  Q  N  G  Q  Y  K  S  E -

AACTGTGTGGGAAATAGAAATCCTTTTGCCCCTGACAGGCCACCTGAGACTCATGCTGAT
481   ---------+---------+---------+---------+---------+---------+ 540
a      N  C  V  G  N  R  N  P  F  A  P  D  R  P  P  E  T  H  A  D -

TATCTCTTGAGAACTGGACAGGTTGTAGATATTTCAGACACCATATACCCGAGGAACCCT
541   ---------+---------+---------+---------+---------+---------+ 600
a      Y  L  L  R  T  G  Q  V  V  D  I  S  D  T  I  Y  P  R  N  P -

GCCATGTGTAGTGAAGAAGCCAGATTGAAGTCATTTCAGAACTGGCCGGACTATGCTCAT
601   ---------+---------+---------+---------+---------+---------+ 660
a      A  M  C  S  E  E  A  R  L  K  S  F  Q  N  W  P  D  Y  A  H -
```

Fig. 4 (pg. 1 of 3)

MOUSE xiap

```
     TTAACCCCCAGAGAGTTAGCTAGTGCTGGCCTCTACTACACAGGGGCTGATGATCAAGTG
 661 ---------+---------+---------+---------+---------+---------+ 720
a     L  T  P  R  E  L  A  S  A  G  L  Y  Y  T  G  A  D  D  Q  V  -

CAATGCTTTTGTTGTGGGGAAAACTGAAAAATTGGGAACCCTGTGATCGTGCCTGGTCA
 721 ---------+---------+---------+---------+---------+---------+ 780
a     Q  C  F  C  C  G  G  K  L  K  N  W  E  P  C  D  R  A  W  S  -

GAACACAGGAGACACTTTCCCAATTGCTTTTTTGTTTTGGGCCGGAACGTTAATGTTCGA
 781 ---------+---------+---------+---------+---------+---------+ 840
a     E  H  R  R  H  F  P  N  C  F  F  V  L  G  R  N  V  N  V  R  -

AGTGAATCTGGTGTGAGTTCTGATAGGAATTTCCCAAATTCAACAAACTCTCCAAGAAAT
 841 ---------+---------+---------+---------+---------+---------+ 900
a     S  E  S  G  V  S  S  D  R  N  F  P  N  S  T  N  S  P  R  N  -

CCAGCCATGGCAGAATATGAAGCACGGATCGTTACTTTTGGAACATGGATATACTCAGTT
 901 ---------+---------+---------+---------+---------+---------+ 960
a     P  A  M  A  E  Y  E  A  R  I  V  T  F  G  T  W  I  Y  S  V  -

AACAAGGAGCAGCTTGCAAGAGCTGGATTTTATGCTTTAGGTGAAGGCGATAAAGTGAAG
 961 ---------+---------+---------+---------+---------+---------+ 1020
a     N  K  E  Q  L  A  R  A  G  F  Y  A  L  G  E  G  D  K  V  K  -

TGCTTCCACTGTGGAGGAGGGCTCACGGATTGGAAGCCAAGTGAAGACCCCTGGGACCAG
1021 ---------+---------+---------+---------+---------+---------+ 1080
a     C  F  H  C  G  G  G  L  T  D  W  K  P  S  E  D  P  W  D  Q  -

CATGCTAAGTGCTACCCAGGGTGCAAATACCTATTGGATGAGAAGGGGCAAGAATATATA
1081 ---------+---------+---------+---------+---------+---------+ 1140
a     H  A  K  C  Y  P  G  C  K  Y  L  L  D  E  K  G  Q  E  Y  I  -

AATAATATTCATTTAACCCATCCACTTGAGGAATCTTTGGGAAGAACTGCTGAAAAAACA
1141 ---------+---------+---------+---------+---------+---------+ 1200
a     N  N  I  H  L  T  H  P  L  E  E  S  L  G  R  T  A  E  K  T  -

CCACCGCTAACTAAAAAAATCGATGATACCATCTTCCAGAATCCTATGGTGCAAGAAGCT
1201 ---------+---------+---------+---------+---------+---------+ 1260
a     P  P  L  T  K  K  I  D  D  T  I  F  Q  N  P  M  V  Q  E  A  -

ATACGAATGGGATTTAGCTTCAAGGACCTTAAGAAAACAATGGAAGAAAAAATCCAAACA
1261 ---------+---------+---------+---------+---------+---------+ 1320
a     I  R  M  G  F  S  F  K  D  L  K  K  T  M  E  E  K  I  Q  T  -

TCCGGGAGCAGCTATCTATCACTTGAGGTCCTGATTGCAGATCTTGTGAGTGCTCAGAAA
1321 ---------+---------+---------+---------+---------+---------+ 1380
a     S  G  S  S  Y  L  S  L  E  V  L  I  A  D  L  V  S  A  Q  K  -
```

Fig. 4 (pg. 2 of 3)

MOUSE xiap

```
       GATAATACGGAGGATGAGTCAAGTCAAACTTCATTGCAGAAAGACATTAGTACTGAAGAG
1381   ------------+---------+---------+---------+---------+---------+ 1440
a       D  N  T  E  D  E  S  S  Q  T  S  L  Q  K  D  I  S  T  E  E    -

CAGCTAAGGCGCCTACAAGAGGAGAAGCTTTCCAAAATCTGTATGGATAGAAATATTGCT
1441   ------------+---------+---------+---------+---------+---------+ 1500
a       Q  L  R  R  L  Q  E  E  K  L  S  K  I  C  M  D  R  N  I  A    -

ATCGTTTTTTTTCCTTGTGGACATCTGGCCACTTGTAAACAGTGTGCAGAAGCAGTTGAC
1501   ------------+---------+---------+---------+---------+---------+ 1560
a       I  V  F  F  P  C  G  H  L  A  T  C  K  Q  C  A  E  A  V  D    -

AAATGTCCCATGTGCTACACCGTCATTACGTTCAACCAAAAAATTTTTATGTCTTAGTGG
1561   ------------+---------+---------+---------+---------+---------+ 1620
a       K  C  P  M  C  Y  T  V  I  T  F  N  Q  K  I  F  M  S  *       -

GGCACCACATGTTATGTTCTTCTTGCTCTAATTGAATGTGTAATGGGAGCGAACTTTAAG
1621   ------------+---------+---------+---------+---------+---------+ 1680
a                                                                       -

TAATCCTGCATTTGCATTCCATTAGCATCCTGCTGTTTCCAAATGGAGACCAATGCTAAC
1681   ------------+---------+---------+---------+---------+---------+ 1740
a                                                                       -

AGCACTGTTTCCGTCTAAACATTCAATTTCTGGATCTTTCGAGTTATCAGCTGTATCATT
1741   ------------+---------+---------+---------+---------+---------+ 1800
a                                                                       -

TAGCCAGTGTTTTACTCGATTGAAACCTTAGACAGAGAAGCATTTTATAGCTTTTCACAT
1801   ------------+---------+---------+---------+---------+---------+ 1860
a                                                                       -

GTATATTGGTAGTACACTGACTTGATTTCTATATGTAAGTGAATTCATCACCTGCATGTT
1861   ------------+---------+---------+---------+---------+---------+ 1920
a                                                                       -

TCATGCCTTTTGCATAAGCTTAACAAATGGAGTGTTCTGTATAAGCATGGAGATGTGATG
1921   ------------+---------+---------+---------+---------+---------+ 1980
a                                                                       -

GAATCTGCCCAATGACTTTAATTGGCTTATTGTAAACACGGAAAGAACTGCCCCACGCTG
1981   ------------+---------+---------+---------+---------+---------+ 2040
a                                                                       -

CTGGGAGGATAAAGATTGTTTTAGATGCTCACTTCTGTGTTTTAGGATTCTGCCCATTTA
2041   ------------+---------+---------+---------+---------+---------+ 2100
```

Fig. 4 (pg. 3 of 3)

Alignment of BIR (Baculoviral IAP Repeats) Domains

Baculovirus
  Cp_iap           Cydia pomonella
  Op_iap           Orgyia pseudotsugata

Human
  xiap             IAP on X chromosome
  hiap1, hiap2    two different human IAP genes

Mouse
  m-xiap          mouse homologue of human xiap gene

Insect
  diap            Drosophilia IAP gene, not clearly a homologue of xiap or hiap note on consensus: The consensus line represents amino acids or very similar amino acids which are present in 14 of the 19 BIR sequences at each position. Capitalized residues are those that are in the consensus sequence.

```
              1                                                                    68
Op_iap-1   kaaRLgTYtn WPvqf.leps rMAasGFYYl GrgDeVrCaf CkveitnWvr gDdpetdHkr waPqCpFV
Cp_iap-l   eevRLnTFek WPvsf.lspe tMAknGFYYl GrsDeVrCaf CkveimrWke gEdpaadHkk waPqCpFV
hiap-2     eanRLvTFkd WPnpn.itpq aLAkAGFYYl nrlDhVkCvw CngviakWek nDnafeeHkr ffPqCprV
n-xiap-1   efnRLkTFan FPssspvsas tLArAGFLYt GegDtVqCFs ChaaidrWqy gDsavgrHrr isPnCrFI
hiap-1     efnRLkTFan FPsgspvsas tLArAGFLYt GegDtVrCFs ChaavdrWqy gDsavgrHrk vsPnCrFI
hiap1-1    elyRMsTYst FPagvpvser sLArAGFYYt GvnDkVkCFc Cglmldnwkr gDsptekHkk lyPsCrFV
hiap2-1    elyRMsTYst FPagvpvser sLArAGFYYt GvnDkVkCFc CglmldnWkl gDspiqkHkq lyPsCsFI
m-xiap-2   eeaRLksFqn WPdyahltpr eLAsAGLLYt GadDqVqCFc CggklknWep cDrawseHrr hfPnCfFv
xiap-2     eeaRLksFqn WPdyahltpr eLAsAGLLYt GigDqVqCFc CggklknWep cDrawseHrr hfPnCfFV
hiap1-2    enaRLlTFqt WP.ltflspt dLArAGFYYi GpgDrVaCFa CggklsnWep kDnamseHlr hfPkCpFI
hiap2-2    eeaRFlTYhm WP.ltflsps eLArAGFYYi GpgDrVaCFa CggklsnWep kDdamseHrr hfPnCpFl
m-xiap-3   yeaRivTFgt Wiysv..nke qLArAGFYal GegDkVkCFh CgggltdWkp sEdpwdqHak cyPgCkYl
xiap-3     yeaRifTFgt Wiysv..nke qLArAGFYal GegDkVkCFh CgggltdWkp sEdpweqHak wyPgCkYl
hiap1-3    haaRFkTFfn WPssvlvnpe qLAsAgFYYv GnsDdVkCFc CdgglrcWes gDdpwvqHak wfPrCeYl
hiap2-3    haaRMrTFmy WPssvpvqpe qLAsAGFYYv GrnDdVkCFg CdgglrcWes gDdpwveHak wfPrCeFl
Op_iap-2   eaaRLrTFae WPrglkqrpe eLAeAGFFYt GqgDktrCFc CdgglkdWep dDapwqqHar wydrCeYV
Cp_iap-2   eaaRvksFhn WPrcmkqrpe qMAdAGFFYt GygDntkCFy cdgglkdWep eDvpweqHvr wfdrCaYV
diap-3     vdaRLrTFtd WPisniqpas aLAqAGLYYq kigDqVrCFh CniglrsWqk eDepwfeHak wsPkCqFV
diap-1     esvRLaTFge WPlnapvsae dLvanGFF.. Gtwmeaecdf ChvridrWey gDlvaerHrr ssPiCsmV
Consensus  ---RL-TF-- WP-------- -LA-AGFYY- G--D-V-CF- C------W-- -D-----H-- --P-C-FV
```

Fig. 5

```
            1                                                                50
   cp-iap   ..........  ..........  ..........  ..[..........  ..........]
     diap   ..........  ..........  mtelgMe[lEs  vRLaTFgeWP   lnaPVSaedL]
   m-xiap   ...mtfnsfe  gtrtfvladt  nkdeEFve[EF  nRLkTFanFP   sssPVSastL]
     xiap   ...mtfnsfe  gsktcvpadi  nkeeEFve[EF  nRLkTFanFP   sgsPVSastL]
    hiap1   mnivensifl  snlmksantf  elkyDLsc[EL  yRMsTYstFP   agvPVSersL]
    hiap2   ...medstil  sdwtns.nkq  kmkyDFsc[EL  iRMsTYstFP   agvPVSersL]
consensus   ----------  ----------  -----F--E-   -RL-TF--FP   ---PVS---L 51                  BIR 1                                       100
   cp-iap  [..........  ..........  ..........  ..........   ..........]
     diap  [vanGFFaTGk  wleaeChfCh  vriDrWeyGD  qvaerHrrss   PiCsmVla..]
   m-xiap  [ARAGFLYTGe  gDtVqCFsCh  aaiDrWqyGD  SavgrHrris   PnCrFIngFy]
     xiap  [ARAGFLYTGe  gDtVrCFsCh  aavDrWqyGD  SavgrHrkvs   PnCrFIngFY]
    hiap1  [ARAGFYYTGv  nDkVkCFcCg  lmlDnWkrGD  SptekHkkly   PsCrFVqsLn]
    hiap2  [ARAGFYYTGv  nDkVkCfcCg  lmlDnWklGD  SpigkHkqly   PsCsFIqnLV]
consensus  [ARAGF-YTG-  -D-V-CF-C-  ---D-W--GD  S----H----   P-C-FI----]

101                                                             150
   cp-iap   ..........  ..........  ..........  ..........   ..........
     diap   ..........  ..........  ..........  .........P   nhcgnvprsq
   m-xiap   ..........  ......feng  aaqStnpgiq  ngqyksenCv   gnrnpfapdR
     xiap   ..........  ......lens  atqStnsgiq  ngqykvenYl   gsrdhfaldR
    hiap1   svnnleatsq  ptfpssvths  .thSllpgte  nsgyfrgsYs   nspsnpvnsR
    hiap2   s.aslgstsk  nt..spmrns  fahSlsptle  hsslfsgsYs   slppnplnsR
consensus   ----------  ----------  ---S------  --------Y-   ---------R 151                                                             200
   cp-iap   ..........  ........mSD  lrl.......  ..[EEvRLnTF  ekWPv.sFLs]
     diap   esDnegnsvv  dspescscpD  lll.......  ..[EanrLvTF  kdWPn.pnit]
   m-xiap   ppEthadyll  rtgqvvDiSD  tiyprnp.aM  cs[EEARLksF  qnWPdyahLt]
     xiap   psEthadyll  rtgqvvDiSD  tiyprnp.aM  yc[EEARLksF  qnWPdyahLt]
    hiap1   anq.......  ......EfSa  lmrssypcpM  nn[EnARLlTF  qtWP.LtfLs]
    hiap2   avE.......  ......DiSs  srtnpysyaM  st[EEARFlTY  hmWP.ltfLs]
consensus   --E-------  ------D-SD  ---------M   --[EEARL-TF  --WP----L-]

201       BIR 2                                                 250
   cp-iap  [PetMAknGFY  YlGrsDeVrC  afCkveimrW  kegEdpaaDH   kkwaPqCPPV]
     diap  [PqaLakAGFY  YlnrlDhVkC  vwCnGviakW  EknDnAfeEH   rRHFPnCfFV]
   m-xiap  [PrELAsAGLY  YtGadDqVqC  FcCGGKLkNW  EPcDrAwSEH   rRHFPnCfFV]
     xiap  [PrELAsAGLY  YtGigDqVqC  FcCGGKLkNW  EPcDrAwSEH   rRHFPNCfFV]
    hiap1  [PtDLArAGFY  YiGpgDrVaC  FaCGGKLsNW  EPkDnAmSEH   lRHFPkCPFI]
    hiap2  [PsELArAGFY  YiGpgDrVaC  FaCGGKLsNW  EPkDdAmSEH   rRHFPnCPFl]
consensus  [P-ELA-AGFY  Y-G--D-V-C  F-CGGKL-NW  EP-D-A-SEH   -RHFP-CPFV]

251                                              BIR 3          300
   cp-iap   kgidvcgsiv  ttnniqnttt  hdtiigPahP  kyAh[eaARvk   sFhnWPrcmk]
     diap   qmgplie.fa  tgknldelgi  qpttl.PlrP  kyAc[vdARlr   TFtdWPiSnI]
   m-xiap   lgrnvnvrse  s.gvssdrnF  pnStnsPrNP  aMAe[yeARiv   TFgtWiyS..]
     xiap   lgrnlnirse  sdavssdrnF  pnStnlPrNP  sMAd[yeARif   TFgtWiyS..]
    hiap1   ..........  enqlqdtsrY  tvS.....Nl  sNqt[haARfk   TFfnWPsSvl]
    hiap2   ..........  ensl.etlrF  siS.....Nl  sMqt[haARmr   TFmyWPsSvp]
consensus   ----------  ---------F  --S---P-NP  -MA-[--AR--   TF--WP-S--]
```

Fig. 6 (pg. 1 of 3)

```
                               BIR 3
           301                                                         350
  cp-iap   qrpEQMAdAG FFYtGyGDnt KCFyCdGGLk dWepeDyPWe QHvrWFdrCa
    diap   qpasaLAqAG LYYqkiGDqv rCFhCnigLr sWqkeDEPWf eHAKWsPkCq
  m-xiap   VnkEQLArAG FYalGeGDkV KCFhCgGGLt dWkpsEDPWd QHAKcYPgCk
    xiap   VnkEQLArAG FYalGeGDkV KCFhCgGGLt dWkpsEDPWd QHAKWYPgCk
   hiap1   VnpEQLAsAG FYYvGnsDdV KCFcCdGGLr cWesgDDPwv QHAKWFPrCe
   hiap2   VqpEQLAsAG FYYvGnsDdV KCFgCdGGLr cWesgDDPWv eHAKWFPrCe
consensus  V--EQLA-AG FYY-G-GD-V KCF-C-GGL- -W---DDPW- QHAKWFP-C-

351                                                         400
  cp-iap   YvqlvKGrDY VqkVit.... .......... ....e..... ..........
    diap   FvllaKGpaY VseVlattaa nassqpaTap aptlq..... ..........
  m-xiap   YLldeKGQEY InnIhlthp. LeEsLgrTae kt........ .....Ppltk
    xiap   YLleqKGQEY InnIhlths. LeEcLvrTte kt........ .....Psltr
   hiap1   YLiriKGQEY IrqVqasyph LlEqLlsTsd spgdenaess iihlePgedh
   hiap2   FLirmKGQEF VdeIggryph LlEqLlsTsd ttgeenadpp iihfgPgess
consensus  YL---KGQEY ---------- L-E-L--T-- ---------- -----P----

401                                                         450
  cp-iap   ..acVLpge. .......... .......... .......... ..........
    diap   ..adVLmdea pakeAltLGi dggvVrnaiq rKllssGcaF stldeLlhDi
  m-xiap   kiDdtifqnP mVqeAirMGF sfkdlKktme eKIqtsGssY lslevLIaDL
    xiap   riDdtifgnP mVqeAirMGF afkdIKkime eKIqisGsnY kslevLVaDL
   hiap1   seDaIMmntP vInaAveMGF srslVKqtvq rKIlatGenY rlvndLVlDL
   hiap2   seDaVMmntP vVksAleMGF nrdlVKqtvl sKIlttGenY ktvndiVsaL
consensus  --D-V----P -V--A--MGF ----VK---- -KI---G--Y -----LV-DL 451                                                         500
  cp-iap   .......... .......... .......... .......... ..........
    diap   fddagagaal Evreppe... .......... .......... ..........
  m-xiap   vsAqkDnteD E......... .......... .......... ..........
    xiap   vnAqkDsmqD E......... .......... .......... ..........
   hiap1   lnAedEireE Ererateeke sndlllirkn rmalfqhltc vipildsllt
   hiap2   lnAedEkreE Ekekqaeema sddlslirkn rmalfqqltc vlpildnllk
consensus  --A------- E--------- ---------- ---------- ----------

501                                                         550
  cp-iap   .......... .......... ..nttvstaa pvsepipe.. ..........
    diap   .......... ...psapfie pcqattskaa svpipvadsi pakpqaaeav
  m-xiap   .......... ....ssQtsL Q......... .......... ..........
    xiap   .......... ....ssQtsL Q......... .......... ..........
   hiap1   agiineqehd vikqktQtsL Qarelidtil vkgniaatvf rnslqeaeav
   hiap2   anvinkqehd iikqktQipL Qarelidtiw vkgnaaanif knclkeidst
consensus  ---------- ------Q--L Q--------- ---------- ----------
```

Fig. 6 (pg. 2 of 3)

```
             551                            RING ZINC FINGER     600
   cp-iap  ...tki....  ..........  .....Ekepq  veDskLCKIC  yveEciVcFV
     diap  sniskitdei  qkmsvstpng  nlSlEEenRq  LkDarLCKVC  LDeEVgVVFl
   m-xiap  ..........  .........k  diStEEQLRR  LqEEkLsKIC  MDrnIaIVFf
     xiap  ..........  .........k  eiStEEQLRR  LqEEkLCKIC  MDrnIaIVFV
    hiap1  lyehlfvqqd  ikyiptedvs  dlpvEEQLRR  LpEErtCKVC  MDkEVsIVFI
    hiap2  lyknlfvdkn  mkyiptedvs  glSlEEQLRR  LqEErtCKVC  MDkEVsVVFI
consensus  ----------  ----------  --S-EEQLRR  L-EE-LCK-C  MD-EV--VF- 601                                      635
   cp-iap  PCGHvVaCak  CAlSVdKCPM  CRkIVtsvlk  vYFS.
     diap  PCGHLatCnq  CApSVanCPM  CRadIkgfvr  tFLS*
   m-xiap  PCGHLatCkq  CAeaVdKCPM  CytVItfnqk  iFMS*
     xiap  PCGHLVtCkq  CAeaVdKCPM  CytVItfkqk  iFMS*
    hiap1  PCGHLVvCkd  CApSlrKCPi  CRstIkgtvr  tFLS*
    hiap2  PCGHLVvCge  CCpSlrKCPi  CRgIIkgtvr  tFLS.
consensus  PCGHLV-C--  CA-SV-KCPM  CR--I-----  -FLS-
```

Fig. 6 (pg. 3 of 3)

Alignment of RZF (Ring Zinc Finger) Domains

Baculovirus
  Cp_iap                 Cydia pomonella
  Op_iap                 Orgyia pseudotsugata
Human
  xiap                   IAP on X chromosome
  hiap1, hiap2       two different human IAP genes
Mouse
  m-xiap                 mouse homologue of human xiap gene
Insect
  diap                   Drosophilia IAP gene, not clearly a homologue of xiap or hiap note on consensus:    The consensus line represents amino acids or very similar amino acids which are present in 6 of the 7 RZF sequences at each position. Capitalized residues are those that are in the consensus sequence.

```
                 1                                              46
hiap2      EqlrrlqEer  tCKVCMdkev  sVvFiPCGHl  vvCqeCApsl  rkCPiC
hiap1      EqlrrlpEer  tCKVCMdkev  sIvFiPCGHl  vvCkdCApsl  rkCPiC
m-xiap     EqlrrlqEek  lsKICMdrni  aIvFfPCGHl  atCkqCAeav  dkCPmC
diap       EqlrrlqEek  lCKICMdrni  aIvFvPCGHl  vtCkqCAeav  dkCPmC
diap       EenrqlkDar  lCKVCLdeev  gVvFlPCGHl  atCnqCApsv  anCPmC
Cp_iap     EkepqveDsk  lCKICyveec  iVcFvPCGHv  vaCakCAlsv  dkCPmC
Op_iap     aveaevaDdr  lCKICLgaek  tVcFvPCGHv  vaCgkCAagv  ttCPvC
consensus  E------E--  -CKICM----  -V-F-PCGH-  --C--CA---  --CP-C
```

Fig. 7

SEQUENCE LISTING

```
(1) GENERAL INFORMATION:

(iii) NUMBER OF SEQUENCES: 38

(2) INFORMATION FOR SEQ ID NO:1:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (ix) FEATURE:
        (D) OTHER INFORMATION: Xaa at positons 2, 3, 4, 5,
            6, 7, 9, 10, 11, 17, 18, 19, 20, 21, 23, 25, 30, 31, 32, 34,
            35,38, 39, 40, 41, 42, and 45 may be any amino acid.  Xaa at
            positon 8 is Glu or Asp.  Xaa at positions 14 & 22 is Val or
            Ile.

(xi) SEQUENCE DESCRIPTION: SEQ ID NO:1:

Glu Xaa Xaa Xaa Xaa Xaa Xaa Xaa Xaa Xaa Xaa Cys Lys Xaa Cys Met
   1               5                   10                  15

Xaa Xaa Xaa Xaa Xaa Xaa Xaa Phe Xaa Pro Cys Gly His Xaa Xaa Xaa
                   20                  25                  30

Cys Xaa Xaa Cys Ala Xaa Xaa Xaa Xaa Xaa Cys Pro Xaa Cys
               35                  40                  45

(2) INFORMATION FOR SEQ ID NO:2:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (ix) FEATURE:
        (D) OTHER INFORMATION: Xaa at positions 1, 2, 3,
            6, 9, 10, 14, 15, 18, 19, 20, 21, 24, 30, 32, 33, 35, 37,
            40, 42, 43, 44, 45, 46, 47, 49, 50, 51, 53, 54, 55, 56,
            57, 59, 60, 61, 62, 64 and 66 may be any amino acid.  Xaa
            at positions 13, 16 and 17 may be any amino acid or may
            be absent.
```

(xi) SEQUENCE DESCRIPTION: SEQ ID NO:2:

Xaa Xaa Xaa Arg Leu Xaa Thr Phe Xaa Xaa Trp Pro Xaa Xaa Xaa Xaa
1               5                   10                  15

Xaa Xaa Xaa Xaa Xaa Leu Ala Xaa Ala Gly Phe Tyr Tyr Xaa Gly Xaa
            20                  25                  30

Xaa Asp Xaa Val Xaa Cys Phe Xaa Cys Xaa Xaa Xaa Xaa Xaa Xaa Trp
        35                  40                  45

Xaa Xaa Xaa Asp Xaa Xaa Xaa Xaa Xaa His Xaa Xaa Xaa Xaa Pro Xaa
    50                  55                  60

Cys Xaa Phe Val
65

(2) INFORMATION FOR SEQ ID NO:3:

(i) SEQUENCE CHARACTERISTICS:
        (A) LENGTH: 2540 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:3:

```
GAAAAGGTGG ACAAGTCCTA TTTTCAAGAG AAGATGACTT TTAACAGTTT TGAAGGATCT      60

AAAACTTGTG TACCTGCAGA CATCAATAAG GAAGAAGAAT TTGTAGAAGA GTTTAATAGA     120

TTAAAAACTT TTGCTAATTT TCCAAGTGGT AGTCCTGTTT CAGCATCAAC ACTGGCACGA     180

GCAGGGTTTC TTTATACTGG TGAAGGAGAT ACCGTGCGGT GCTTTAGTTG TCATGCAGCT     240

GTAGATAGAT GGCAATATGG AGACTCAGCA GTTGGAAGAC ACAGGAAAGT ATCCCCAAAT     300

TGCAGATTTA TCAACGGCTT TTATCTTGAA AATAGTGCCA CGCAGTCTAC AAATTCTGGT     360

ATCCAGAATG GTCAGTACAA AGTTGAAAAC TATCTGGGAA GCAGAGATCA TTTTGCCTTA     420

GACAGGCCAT CTGAGACACA TGCAGACTAT CTTTTGAGAA CTGGGCAGGT TGTAGATATA     480

TCAGACACCA TATACCCGAG GAACCCTGCC ATGTATTGTG AAGAAGCTAG ATTAAAGTCC     540

TTTCAGAACT GGCCAGACTA TGCTCACCTA ACCCCAAGAG AGTTAGCAAG TGCTGGACTC     600

TACTACACAG GTATTGGTGA CCAAGTGCAG TGCTTTTGTT GTGGTGGAAA ACTGAAAAAT     660

TGGGAACCTT GTGATCGTGC CTGGTCAGAA CACAGGCGAC ACTTTCCTAA TTGCTTCTTT     720

GTTTTGGGCC GGAATCTTAA TATTCGAAGT GAATCTGATG CTGTGAGTTC TGATAGGAAT     780

TTCCCAAATT CAACAAATCT TCCAAGAAAT CCATCCATGG CAGATTATGA AGCACGGATC     840

TTTACTTTTG GGACATGGAT ATACTCAGTT AACAAGGAGC AGCTTGCAAG AGCTGGATTT     900

TATGCTTTAG GTGAAGGTGA TAAAGTAAAG TGCTTTCACT GTGGAGGAGG GCTAACTGAT     960

TGGAAGCCCA GTGAAGACCC TTGGGAACAA CATGCTAAAT GGTATCCAGG GTGCAAATAT    1020

CTGTTAGAAC AGAAGGGACA AGAATATATA AACAATATTC ATTTAACTCA TTCACTTGAG    1080

GAGTGTCTGG TAAGAACTAC TGAGAAAACA CCATCACTAA CTAGAAGAAT TGATGATACC    1140

ATCTTCCAAA ATCCTATGGT ACAAGAAGCT ATACGAATGG GGTTCAGTTT CAAGGACATT    1200

AAGAAAATAA TGGAGGAAAA AATTCAGATA TCTGGGAGCA ACTATAAATC ACTTGAGGTT    1260

CTGGTTGCAG ATCTAGTGAA TGCTCAGAAA GACAGTATGC AAGATGAGTC AAGTCAGACT    1320

TCATTACAGA AAGAGATTAG TACTGAAGAG CAGCTAAGGC GCCTGCAAGA GGAGAAGCTT    1380

TGCAAAATCT GTATGGATAG AAATATTGCT ATCGTTTTTG TTCCTTGTGG ACATCTAGTC    1440

ACTTGTAAAC AATGTGCTGA AGCAGTTGAC AAGTGTCCCA TGTGCTACAC AGTCATTACT    1500
```

-continued

```
TTCAAGCAAA AAATTTTTAT GTCTTAATCT AACTCTATAG TAGGCATGTT ATGTTGTTCT    1560

TATTACCCTG ATTGAATGTG TGATGTGAAC TGACTTTAAG TAATCAGGAT TGAATTCCAT    1620

TAGCATTTGC TACCAAGTAG GAAAAAAAAT GTACATGGCA GTGTTTTAGT TGGCAATATA    1680

ATCTTTGAAT TCTTGATTT TCAGGGTAT TAGCTGTATT ATCCATTTTT TTTACTGTTA      1740

TTTAATTGAA ACCATAGACT AAGAATAAGA AGCATCATAC TATAACTGAA CACAATGTGT    1800

ATTCATAGTA TACTGATTTA ATTTCTAAGT GTAAGTGAAT TAATCATCTG GATTTTTAT     1860

TCTTTTCAGA TAGGCTTAAC AAATGGAGCT TTCTGTATAT AAATGTGGAG ATTAGAGTTA    1920

ATCTCCCCAA TCACATAATT TGTTTTGTGT GAAAAAGGAA TAAATTGTTC CATGCTGGTG    1980

GAAAGATAGA GATTGTTTTT AGAGGTTGGT TGTTGTGTTT TAGGATTCTG TCCATTTTCT    2040

TGTAAAGGGA TAAACACGGA CGTGTGCGAA ATATGTTTGT AAAGTGATTT GCCATTGTTG    2100

AAAGCGTATT TAATGATAGA ATACTATCGA GCCAACATGT ACTGACATGG AAAGATGTCA    2160

GAGATATGTT AAGTGTAAAA TGCAAGTGGC GGGACACTAT GTATAGTCTG AGCCAGATCA    2220

AAGTATGTAT GTTGTTAATA TGCATAGAAC GAGAGATTTG GAAAGATATA CACCAAACTG    2280

TTAAATGTGG TTTCTCTTCG GGGAGGGGGG GATTGGGGGA GGGGCCCCAG AGGGGTTTTA    2340

GAGGGGCCTT TTCACTTTCG ACTTTTTTCA TTTTTGTTCTG TTCGGATTTT TTATAAGTAT   2400

GTAGACCCCG AAGGGTTTTA TGGGAACTAA CATCAGTAAC CTAACCCCCG TGACTATCCT    2460

GTGCTCTTCC TAGGGAGCTG TGTTGTTTCC CACCCACCAC CCTTCCCTCT GAACAAATGC    2520

CTGAGTGCTG GGGCACTTTN                                                2540
```

(2) INFORMATION FOR SEQ ID NO:4:

(i) SEQUENCE CHARACTERISTICS:
        (A) LENGTH: 497 amino acids
        (B) TYPE: amino acid
        (C) STRANDEDNESS: unknown
        (D) TOPOLOGY: both (ii) MOLECULE TYPE: protein (xi) SEQUENCE DESCRIPTION: SEQ ID NO:4:

```
Met Thr Phe Asn Ser Phe Glu Gly Ser Lys Thr Cys Val Pro Ala Asp
  1               5                  10                  15

Ile Asn Lys Glu Glu Phe Val Glu Phe Asn Arg Leu Lys Thr
             20                  25                  30

Phe Ala Asn Phe Pro Ser Gly Ser Pro Val Ser Ala Ser Thr Leu Ala
             35                  40                  45

Arg Ala Gly Phe Leu Tyr Thr Gly Glu Gly Asp Thr Val Arg Cys Phe
         50                  55                  60

Ser Cys His Ala Ala Val Asp Arg Trp Gln Tyr Gly Asp Ser Ala Val
 65                  70                  75                  80

Gly Arg His Arg Lys Val Ser Pro Asn Cys Arg Phe Ile Asn Gly Phe
                     85                  90                  95

Tyr Leu Glu Asn Ser Ala Thr Gln Ser Thr Asn Ser Gly Ile Gln Asn
                100                 105                 110

Gly Gln Tyr Lys Val Glu Asn Tyr Leu Gly Ser Arg Asp His Phe Ala
            115                 120                 125

Leu Asp Arg Pro Ser Glu Thr His Ala Asp Tyr Leu Leu Arg Thr Gly
        130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
```

```
                    165                 170                 175
    Ala His Leu Thr Pro Arg Glu Leu Ala Ser Ala Gly Leu Tyr Tyr Thr
                180                 185                 190

Gly Ile Gly Asp Gln Val Gln Cys Phe Cys Gly Gly Lys Leu Lys
            195                 200                 205

Asn Trp Glu Pro Cys Asp Arg Ala Trp Ser Glu His Arg His Phe
        210                 215                 220

Pro Asn Cys Phe Phe Val Leu Gly Arg Asn Leu Asn Ile Arg Ser Glu
    225                 230                 235                 240

Ser Asp Ala Val Ser Ser Asp Arg Asn Phe Pro Asn Ser Thr Asn Leu
                    245                 250                 255

Pro Arg Asn Pro Ser Met Ala Asp Tyr Glu Ala Arg Ile Phe Thr Phe
                260                 265                 270

Gly Thr Trp Ile Tyr Ser Val Asn Lys Glu Gln Leu Ala Arg Ala Gly
                275                 280                 285

Phe Tyr Ala Leu Gly Glu Gly Asp Lys Val Lys Cys Phe His Cys Gly
            290                 295                 300

Gly Gly Leu Thr Asp Trp Lys Pro Ser Glu Asp Pro Trp Glu Gln His
    305                 310                 315                 320

Ala Lys Trp Tyr Pro Gly Cys Lys Tyr Leu Leu Glu Gln Lys Gly Gln
                    325                 330                 335

Glu Tyr Ile Asn Asn Ile His Leu Thr His Ser Leu Glu Glu Cys Leu
                340                 345                 350

Val Arg Thr Thr Glu Lys Thr Pro Ser Leu Thr Arg Arg Ile Asp Asp
                355                 360                 365

Thr Ile Phe Gln Asn Pro Met Val Gln Glu Ala Ile Arg Met Gly Phe
            370                 375                 380

Ser Phe Lys Asp Ile Lys Lys Ile Met Glu Glu Lys Ile Gln Ile Ser
    385                 390                 395                 400

Gly Ser Asn Tyr Lys Ser Leu Glu Val Leu Val Ala Asp Leu Val Asn
                    405                 410                 415

Ala Gln Lys Asp Ser Met Gln Asp Glu Ser Ser Gln Thr Ser Leu Gln
                420                 425                 430

Lys Glu Ile Ser Thr Glu Glu Gln Leu Arg Arg Leu Gln Glu Glu Lys
                435                 440                 445

Leu Cys Lys Ile Cys Met Asp Arg Asn Ile Ala Ile Val Phe Val Pro
    450                 455                 460

Cys Gly His Leu Val Thr Cys Lys Gln Cys Ala Glu Ala Val Asp Lys
    465                 470                 475                 480

Cys Pro Met Cys Tyr Thr Val Ile Thr Phe Lys Gln Lys Ile Phe Met
                    485                 490                 495

Ser (2) INFORMATION FOR SEQ ID NO:5:

(i) SEQUENCE CHARACTERISTICS:
        (A) LENGTH: 2676 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:5:

TCCTTGAGAT GTATCAGTAT AGGATTTAGG ATCTCCATGT TGGAACTCTA AATGCATAGA         60

AATGGAAATA ATGGAAATTT TTCATTTTGG CTTTTCAGCC TAGTATTAAA ACTGATAAAA        120
```

```
GCAAAGCCAT GCACAAAACT ACCTCCCTAG AGAAAGGCTA GTCCCTTTTC TTCCCCATTC      180

ATTTCATTAT GAACATAGTA GAAAACAGCA TATTCTTATC AAATTTGATG AAAAGCGCCA      240

ACACGTTTGA ACTGAAATAC GACTTGTCAT GTGAACTGTA CCGAATGTCT ACGTATTCCA      300

CTTTTCCTGC TGGGGTTCCT GTCTCAGAAA GGAGTCTTGC TCGTGCTGGT TTCTATTACA      360

CTGGTGTGAA TGACAAGGTC AAATGCTTCT GTTGTGGCCT GATGCTGGAT AACTGGAAAA      420

GAGGAGACAG TCCTACTGAA AAGCATAAAA AGTTGTATCC TAGCTGCAGA TTCGTTCAGA      480

GTCTAAATTC CGTTAACAAC TTGGAAGCTA CCTCTCAGCC TACTTTTCCT TCTTCAGTAA      540

CACATTCCAC ACACTCATTA CTTCCGGGTA CAGAAAACAG TGGATATTTC CGTGGCTCTT      600

ATTCAAACTC TCCATCAAAT CCTGTAAACT CCAGAGCAAA TCAAGAATTT TCTGCCTTGA      660

TGAGAAGTTC CTACCCCTGT CCAATGAATA ACGAAAATGC CAGATTACTT ACTTTTCAGA      720

CATGGCCATT GACTTTTCTG TCGCCAACAG ATCTGGCACG AGCAGGCTTT TACTACATAG      780

GACCTGGAGA CAGAGTGGCT TGCTTTGCCT GTGGTGGAAA ATTGAGCAAT TGGGAACCGA      840

AGGATAATGC TATGTCAGAA CACCTGAGAC ATTTTCCCAA ATGCCCATTT ATAGAAAATC      900

AGCTTCAAGA CACTTCAAGA TACACAGTTT CTAATCTGAG CATGCAGACA CATGCAGCCC      960

GCTTTAAAAC ATTCTTTAAC TGGCCCTCTA GTGTTCTAGT TAATCCTGAG CAGCTTGCAA     1020

GTGCGGGTTT TTATTATGTG GGTAACAGTG ATGATGTCAA ATGCTTTTGC TGTGATGGTG     1080

GACTCAGGTG TTGGGAATCT GGAGATGATC CATGGGTTCA ACATGCCAAG TGGTTTCCAA     1140

GGTGTGAGTA CTTGATAAGA ATTAAAGGAC AGGAGTTCAT CCGTCAAGTT CAAGCCAGTT     1200

ACCCTCATCT ACTTGAACAG CTGCTATCCA CATCAGACAG CCCAGGAGAT GAAAATGCAG     1260

AGTCATCAAT TATCCATTTG GAACCTGGAG AAGACCATTC AGAAGATGCA ATCATGATGA     1320

ATACTCCTGT GATTAATGCT GCCGTGGAAA TGGGCTTTAG TAGAAGCCTG GTAAAACAGA     1380

CAGTTCAGAG AAAAATCCTA GCAACTGGAG AGAATTATAG ACTAGTCAAT GATCTTGTGT     1440

TAGACTTACT CAATGCAGAA GATGAAATAA GGGAAGAGGA GAGAGAAAGA GCAACTGAGG     1500

AAAAAGAATC AAATGATTTA TTATTAATCC GGAAGAATAG AATGGCACTT TTTCAACATT     1560

TGACTTGTGT AATTCCAATC CTGGATAGTC TACTAACTGC CGGAATTATT AATGAACAAG     1620

AACATGATGT TATTAAACAG AAGACACAGA CGTCTTTACA AGCAAGAGAA CTGATTGATA     1680

CGATTTAGT AAAAGGAAAT ATTGCAGCCA CTGTATTCAG AAACTCTCTG CAAGAAGCTG     1740

AAGCTGTGTT ATATGAGCAT TTATTTGTGC AACAGGACAT AAAATATATT CCCACAGAAG     1800

ATGTTTCAGA TCTACCAGTG GAAGAACAAT TGCGGAGACT ACCAGAAGAA AGAACATGTA     1860

AAGTGTGTAT GGACAAAGAA GTGTCCATAG TGTTTATTCC TTGTGGTCAT CTAGTAGTAT     1920

GCAAAGATTG TGCTCCTTCT TTAAGAAAGT GTCCTATTTG TAGGAGTACA ATCAAGGGTA     1980

CAGTTCGTAC ATTTCTTTCA TGAAGAAGAA CCAAAACATC GTCTAAACTT TAGAATTAAT     2040

TTATTAAATG TATTATAACT TTAACTTTTA TCCTAATTTG GTTTCCTTAA AATTTTTATT     2100

TATTTACAAC TCAAAAAACA TTGTTTTGTG TAACATATTT ATATATGTAT CTAAACCATA     2160

TGAACATATA TTTTTTAGAA ACTAAGAGAA TGATAGGCTT TTGTTCTTAT GAACGAAAAA     2220

GAGGTAGCAC TACAAACACA ATATTCAATC CAAATTTCAG CATTATTGAA ATTGTAAGTG     2280

AAGTAAAACT TAAGATATTT GAGTTAACCT TTAAGAATTT TAAATATTTT GGCATTGTAC     2340

TAATACCGGG AACATGAAGC CAGGTGTGGT GGTATGTACC TGTAGTCCCA GGCTGAGGCA     2400

AGAGAATTAC TTGAGCCCAG GAGTTTGAAT CCATCCTGGG CAGCATACTG AGACCCTGCC     2460

TTTAAAAACN AACAGNACCA AANCCAAACA CCAGGGACAC ATTTCTCTGT CTTTTTTGAT     2520
```

```
CAGTGTCCTA TACATCGAAG GTGTGCATAT ATGTTGAATC ACATTTTAGG GACATGGTGT   2580

TTTTATAAAG AATTCTGTGA GNAAAAATTT AATAAAGCAA CCAAATTACT CTTAAAAAAA   2640

AAAAAAAAAA AAAAAACTCG AGGGGCCCGT ACCAAT                             2676
```

(2) INFORMATION FOR SEQ ID NO:6:

(i) SEQUENCE CHARACTERISTICS:
        (A) LENGTH: 604 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:6:

```
Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
                20                  25                  30

Met Ser Thr Tyr Ser Thr Phe Pro Ala Gly Val Pro Val Ser Glu Arg
            35                  40                  45

Ser Leu Ala Arg Ala Gly Phe Tyr Tyr Thr Gly Val Asn Asp Lys Val
        50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
                100                 105                 110

Phe Pro Ser Ser Val Thr His Ser Thr His Ser Leu Leu Pro Gly Thr
            115                 120                 125

Glu Asn Ser Gly Tyr Phe Arg Gly Ser Tyr Ser Asn Ser Pro Ser Asn
        130                 135                 140

Pro Val Asn Ser Arg Ala Asn Gln Glu Phe Ser Ala Leu Met Arg Ser
145                 150                 155                 160

Ser Tyr Pro Cys Pro Met Asn Asn Glu Asn Ala Arg Leu Leu Thr Phe
                165                 170                 175

Gln Thr Trp Pro Leu Thr Phe Leu Ser Pro Thr Asp Leu Ala Arg Ala
                180                 185                 190

Gly Phe Tyr Tyr Ile Gly Pro Gly Asp Arg Val Ala Cys Phe Ala Cys
            195                 200                 205

Gly Gly Lys Leu Ser Asn Trp Glu Pro Lys Asp Asn Ala Met Ser Glu
        210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
                260                 265                 270

Pro Glu Gln Leu Ala Ser Ala Gly Phe Tyr Tyr Val Gly Asn Ser Asp
            275                 280                 285

Asp Val Lys Cys Phe Cys Cys Asp Gly Gly Leu Arg Cys Trp Glu Ser
        290                 295                 300

Gly Asp Asp Pro Trp Val Gln His Ala Lys Trp Phe Pro Arg Cys Glu
305                 310                 315                 320
```

```
Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Leu Glu Pro Gly Glu
            355                 360                 365

Asp His Ser Glu Asp Ala Ile Met Met Asn Thr Pro Val Ile Asn Ala
        370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
            435                 440                 445

Lys Asn Arg Met Ala Leu Phe Gln His Leu Thr Cys Val Ile Pro Ile
        450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
            515                 520                 525

Gln Asp Ile Lys Tyr Ile Pro Thr Glu Asp Val Ser Asp Leu Pro Val
        530                 535                 540

Glu Glu Gln Leu Arg Arg Leu Pro Glu Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
            595                 600

(2) INFORMATION FOR SEQ ID NO:7:

(i) SEQUENCE CHARACTERISTICS:
        (A) LENGTH: 2580 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:7:

TTAGGTTACC TGAAAGAGTT ACTACAACCC CAAAGAGTTG TGTTCTAAGT AGTATCTTGG      60

TAATTCAGAG AGATACTCAT CCTACCTGAA TATAAACTGA GATAAATCCA GTAAAGAAAG    120

TGTAGTAAAT TCTACATAAG AGTCTATCAT TGATTTCTTT TTGTGGTGGA AATCTTAGTT    180

CATGTGAAGA AATTTCATGT GAATGTTTTA GCTATCAAAC AGTACTGTCA CCTACTCATG    240

CACAAAACTG CCTCCCAAAG ACTTTTCCCA GGTCCCTCGT ATCAAAACAT TAAGAGTATA    300

ATGGAAGATA GCACGATCTT GTCAGATTGG ACAAACAGCA ACAAACAAAA AATGAAGTAT    360

GACTTTTCCT GTGAACTCTA CAGAATGTCT ACATATTCAA CTTTCCCCGC CGGGGTGCCT    420
```

```
GTCTCAGAAA GGAGTCTTGC TCGTGCTGGT TTTTATTATA CTGGTGTGAA TGACAAGGTC        480
AAATGCTTCT GTTGTGGCCT GATGCTGGAT AACTGGAAAC TAGGAGACAG TCCTATTCAA        540
AAGCATAAAC AGCTATATCC TAGCTGTAGC TTTATTCAGA ATCTGGTTTC AGCTAGTCTG        600
GGATCCACCT CTAAGAATAC GTCTCCAATG AGAAACAGTT TTGCACATTC ATTATCTCCC        660
ACCTTGGAAC ATAGTAGCTT GTTCAGTGGT TCTTACTCCA GCCTTCCTCC AAACCCTCTT        720
AATTCTAGAG CAGTTGAAGA CATCTCTTCA TCGAGGACTA ACCCCTACAG TTATGCAATG        780
AGTACTGAAG AAGCCAGATT TCTTACCTAC CATATGTGGC CATTAACTTT TTTGTCACCA        840
TCAGAATTGG CAAGAGCTGG TTTTTATTAT ATAGGACCTG GAGATAGGGT AGCCTGCTTT        900
GCCTGTGGTG GGAAGCTCAG TAACTGGGAA CCAAAGGATG ATGCTATGTC AGAACACCGG        960
AGGCATTTTC CCAACTGTCC ATTTTTGGAA AATTCTCTAG AAACTCTGAG GTTTAGCATT       1020
TCAAATCTGA GCATGCAGAC ACATGCAGCT CGAATGAGAA CATTTATGTA CTGGCCATCT       1080
AGTGTTCCAG TTCAGCCTGA GCAGCTTGCA AGTGCTGGTT TTTATTATGT GGGTCGCAAT       1140
GATGATGTCA AATGCTTTGG TTGTGATGGT GGCTTGAGGT GTTGGGAATC TGGAGATGAT       1200
CCATGGGTAG AACATGCCAA GTGGTTTCCA AGGTGTGAGT TCTTGATACG AATGAAAGGC       1260
CAAGAGTTTG TTGATGAGAT TCAAGGTAGA TATCCTCATC TTCTTGAACA GCTGTTGTCA       1320
ACTTCAGATA CCACTGGAGA AGAAAATGCT GACCCACCAA TTATTCATTT TGGACCTGGA       1380
GAAAGTTCTT CAGAAGATGC TGTCATGATG AATACACCTG TGGTTAAATC TGCCTTGGAA       1440
ATGGGCTTTA ATAGAGACCT GGTGAAACAA ACAGTTCTAA GTAAAATCCT GACAACTGGA       1500
GAGAACTATA AACAGTTAAA TGATATTGTG TCAGCACTTC TTAATGCTGA AGATGAAAAA       1560
AGAGAAGAGG AGAAGGAAAA ACAAGCTGAA GAAATGGCAT CAGATGATTT GTCATTAATT       1620
CGGAAGAACA GAATGGCTCT CTTTCAACAA TTGACATGTG TGCTTCCTAT CCTGGATAAT       1680
CTTTTAAAGG CCAATGTAAT TAATAAACAG GAACATGATA TTATTAAACA AAAAACACAG       1740
ATACCTTTAC AAGCGAGAGA ACTGATTGAT ACCATTTGGG TTAAAGGAAA TGCTGCGGCC       1800
AACATCTTCA AAAACTGTCT AAAAGAAATT GACTCTACAT TGTATAAGAA CTTATTTGTG       1860
GATAAGAATA TGAAGTATAT TCCAACAGAA GATGTTTCAG GTCTGTCACT GGAAGAACAA       1920
TTGAGGAGGT TGCAAGAAGA ACGAACTTGT AAAGTGTGTA TGGACAAAGA AGTTTCTGTT       1980
GTATTTATTC CTTGTGGTCA TCTGGTAGTA TGCCAGGAAT GTGCCCCTTC TCTAAGAAAA       2040
TGCCCTATTT GCAGGGTAT AATCAAGGGT ACTGTTCGTA CATTTCTCTC TTAAAGAAAA        2100
ATAGTCTATA TTTTAACCTG CATAAAAAGG TCTTTAAAAT ATTGTTGAAC ACTTGAAGCC       2160
ATCTAAAGTA AAAAGGGAAT TATGAGTTTT TCAATTAGTA ACATTCATGT TCTAGTCTGC       2220
TTTGGTACTA ATAATCTTGT TTCTGAAAAG ATGGTATCAT ATATTTAATC TTAATCTGTT       2280
TATTTACAAG GGAAGATTTA TGTTTGGTGA ACTATATTAG TATGTATGTG TACCTAAGGG       2340
AGTAGCGTCN CTGCTTGTTA TGCATCATTT CAGGAGTTAC TGGATTTGTT GTTCTTTCAG       2400
AAAGCTTTGA ANACTAAATT ATAGTGTAGA AAAGAACTGG AAACCAGGAA CTCTGGAGTT       2460
CATCAGAGTT ATGGTGCCGA ATTGTCTTTG GTGCTTTTCA CTTGTGTTTT AAAATAAGGA       2520
TTTTTCTCTT ATTTCTCCCC CTAGTTTGTG AGAAACATCT CAATAAAGTG CTTTAAAAAG       2580
```

(2) INFORMATION FOR SEQ ID NO:8:

(i) SEQUENCE CHARACTERISTICS:
        (A) LENGTH: 618 amino acids
        (B) TYPE: amino acid
        (C) STRANDEDNESS: Not Relevant (D) TOPOLOGY: both (ii) MOLECULE TYPE: protein (xi) SEQUENCE DESCRIPTION: SEQ ID NO:8:

```
Met His Lys Thr Ala Ser Gln Arg Leu Phe Pro Gly Pro Ser Tyr Gln
 1               5                  10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Pro Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
    195                 200                 205

Phe Tyr Tyr Ile Gly Pro Gly Asp Arg Val Ala Cys Phe Ala Cys Gly
210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
    275                 280                 285

Gln Leu Ala Ser Ala Gly Phe Tyr Tyr Val Gly Arg Asn Asp Asp Val
290                 295                 300

Lys Cys Phe Gly Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
            340                 345                 350

Pro His Leu Leu Glu Gln Leu Leu Ser Thr Ser Asp Thr Thr Gly Glu
    355                 360                 365

Glu Asn Ala Asp Pro Pro Ile Ile His Phe Gly Pro Gly Glu Ser Ser
370                 375                 380

Ser Glu Asp Ala Val Met Met Asn Thr Pro Val Val Lys Ser Ala Leu
385                 390                 395                 400
```

```
Glu Met Gly Phe Asn Arg Asp Leu Val Lys Gln Thr Val Leu Ser Lys
                405                 410                 415
Ile Leu Thr Thr Gly Glu Asn Tyr Lys Thr Val Asn Asp Ile Val Ser
                420                 425                 430
Ala Leu Leu Asn Ala Glu Asp Glu Lys Arg Glu Glu Lys Glu Lys
            435                 440                 445
Gln Ala Glu Glu Met Ala Ser Asp Asp Leu Ser Leu Ile Arg Lys Asn
    450                 455                 460
Arg Met Ala Leu Phe Gln Gln Leu Thr Cys Val Leu Pro Ile Leu Asp
465                 470                 475                 480
Asn Leu Lys Ala Asn Val Ile Asn Lys Gln Glu His Asp Ile Ile
                485                 490                 495
Lys Gln Lys Thr Gln Ile Pro Leu Gln Ala Arg Glu Leu Ile Asp Thr
                500                 505                 510
Ile Trp Val Lys Gly Asn Ala Ala Ala Asn Ile Phe Lys Asn Cys Leu
        515                 520                 525
Lys Glu Ile Asp Ser Thr Leu Tyr Lys Asn Leu Phe Val Asp Lys Asn
            530                 535                 540
Met Lys Tyr Ile Pro Thr Glu Asp Val Ser Gly Leu Ser Leu Glu Glu
545                 550                 555                 560
Gln Leu Arg Arg Leu Gln Glu Glu Arg Thr Cys Lys Val Cys Met Asp
                565                 570                 575
Lys Glu Val Ser Val Val Phe Ile Pro Cys Gly His Leu Val Val Cys
            580                 585                 590
Gln Glu Cys Ala Pro Ser Leu Arg Lys Cys Pro Ile Cys Arg Gly Ile
                595                 600                 605
Ile Lys Gly Thr Val Arg Thr Phe Leu Ser
610                 615
```

(2) INFORMATION FOR SEQ ID NO:9:

(i) SEQUENCE CHARACTERISTICS:
        (A) LENGTH: 2100 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:9:

```
GACACTCTGC TGGGCGGCGG GCCGCCCTCC TCCGGGACCT CCCCTCGGGA ACCGTCGCCC    60

GCGGCGCTTA GTTAGGACTG GAGTGCTTGG CGCGAAAAGG TGGACAAGTC CTATTTTCCA   120

GAGAAGATGA CTTTTAACAG TTTTGAAGGA ACTAGAACTT TTGTACTTGC AGACACCAAT   180

AAGGATGAAG AATTTGTAGA AGAGTTTAAT AGATTAAAAA CATTTGCTAA CTTCCCAAGT   240

AGTAGTCCTG TTTCAGCATC AACATTGGCG CGAGCTGGGT TTCTTTATAC CGGTGAAGGA   300

GACACCGTGC AATGTTTCAG TTGTCATGCG GCAATAGATA GATGGCAGTA TGGAGACTCA   360

GCTGTTGGAA GACACAGGAG AATATCCCCA AATTGCAGAT TTATCAATGG TTTTTATTTT   420

GAAAATGGTG CTGCACAGTC TACAAATCCT GGTATCCAAA ATGGCCAGTA CAAATCTGAA   480

AACTGTGTGG GAAATAGAAA TCCTTTTGCC CCTGACAGGC CACCTGAGAC TCATGCTGAT   540

TATCTCTTGA GAACTGGACA GGTTGTAGAT ATTTCAGACA CCATATACCC GAGGAACCCT   600

GCCATGTGTA GTGAAGAAGC CAGATTGAAG TCATTTCAGA ACTGGCCGGA CTATGCTCAT   660

TTAACCCCCA GAGAGTTAGC TAGTGCTGGC CTCTACTACA CAGGGGCTGA TGATCAAGTG   720
```

```
CAATGCTTTT GTTGTGGGGG AAAACTGAAA AATTGGGAAC CCTGTGATCG TGCCTGGTCA      780

GAACACAGGA GACACTTTCC CAATTGCTTT TTTGTTTTGG GCCGGAACGT TAATGTTCGA      840

AGTGAATCTG GTGTGAGTTC TGATAGGAAT TTCCCAAATT CAACAAACTC TCCAAGAAAT      900

CCAGCCATGG CAGAATATGA AGCACGGATC GTTACTTTTG AACATGGAT ATACTCAGTT       960

AACAAGGAGC AGCTTGCAAG AGCTGGATTT TATGCTTTAG GTGAAGGCGA TAAAGTGAAG      1020

TGCTTCCACT GTGGAGGAGG GCTCACGGAT TGGAAGCCAA GTGAAGACCC CTGGGACCAG      1080

CATGCTAAGT GCTACCCAGG GTGCAAATAC CTATTGGATG AGAAGGGGCA AGAATATATA     1140

AATAATATTC ATTTAACCCA TCCACTTGAG GAATCTTTGG GAAGAACTGC TGAAAAAACA     1200

CCACCGCTAA CTAAAAAAAT CGATGATACC ATCTTCCAGA ATCCTATGGT GCAAGAAGCT     1260

ATACGAATGG GATTTAGCTT CAAGGACCTT AAGAAAACAA TGGAAGAAAA AATCCAAACA     1320

TCCGGGAGCA GCTATCTATC ACTTGAGGTC CTGATTGCAG ATCTTGTGAG TGCTCAGAAA     1380

GATAATACGG AGGATGAGTC AAGTCAAACT TCATTGCAGA AAGACATTAG TACTGAAGAG     1440

CAGCTAAGGC GCCTACAAGA GGAGAAGCTT TCCAAAATCT GTATGGATAG AAATATTGCT     1500

ATCGTTTTTT TTCCTTGTGG ACATCTGGCC ACTTGTAAAC AGTGTGCAGA AGCAGTTGAC     1560

AAATGTCCCA TGTGCTACAC CGTCATTACG TTCAACCAAA AAATTTTTAT GTCTTAGTGG     1620

GGCACCACAT GTTATGTTCT TCTTGCTCTA ATTGAATGTG TAATGGGAGC GAACTTTAAG     1680

TAATCCTGCA TTTGCATTCC ATTAGCATCC TGCTGTTTCC AAATGGAGAC CAATGCTAAC     1740

AGCACTGTTT CCGTCTAAAC ATTCAATTTC TGGATCTTTC GAGTTATCAG CTGTATCATT     1800

TAGCCAGTGT TTTACTCGAT TGAAACCTTA GACAGAGAAG CATTTTATAG CTTTTCACAT     1860

GTATATTGGT AGTACACTGA CTTGATTTCT ATATGTAAGT GAATTCATCA CCTGCATGTT     1920

TCATGCCTTT TGCATAAGCT TAACAAATGG AGTGTTCTGT ATAAGCATGG AGATGTGATG     1980

GAATCTGCCC AATGACTTTA ATTGGCTTAT TGTAAACACG GAAAGAACTG CCCCACGCTG     2040

CTGGGAGGAT AAAGATTGTT TTAGATGCTC ACTTCTGTGT TTTAGGATTC TGCCCATTTA     2100
```

(2) INFORMATION FOR SEQ ID NO:10:

(i) SEQUENCE CHARACTERISTICS:
        (A) LENGTH: 496 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:10:

```
Met Thr Phe Asn Ser Phe Glu Gly Thr Arg Thr Phe Val Leu Ala Asp
1               5                   10                  15

Thr Asn Lys Asp Glu Glu Phe Val Glu Phe Asn Arg Leu Lys Thr
            20                  25                  30

Phe Ala Asn Phe Pro Ser Ser Pro Val Ser Ala Ser Thr Leu Ala
        35                  40                  45

Arg Ala Gly Phe Leu Tyr Thr Gly Glu Gly Asp Thr Val Gln Cys Phe
    50                  55                  60

Ser Cys His Ala Ala Ile Asp Arg Trp Gln Tyr Gly Asp Ser Ala Val
65                  70                  75                  80

Gly Arg His Arg Arg Ile Ser Pro Asn Cys Arg Phe Ile Asn Gly Phe
                85                  90                  95

Tyr Phe Glu Asn Gly Ala Ala Gln Ser Thr Asn Pro Gly Ile Gln Asn
                100                 105                 110
```

-continued

```
Gly Gln Tyr Lys Ser Glu Asn Cys Val Gly Asn Arg Asn Pro Phe Ala
            115                 120                 125
Pro Asp Arg Pro Pro Glu Thr His Ala Asp Tyr Leu Leu Arg Thr Gly
        130                 135                 140
Gln Val Val Asp Ile Ser Asp Thr Ile Tyr Pro Arg Asn Pro Ala Met
145                 150                 155                 160
Cys Ser Glu Glu Ala Arg Leu Lys Ser Phe Gln Asn Trp Pro Asp Tyr
                165                 170                 175
Ala His Leu Thr Pro Arg Glu Leu Ala Ser Ala Gly Leu Tyr Tyr Thr
            180                 185                 190
Gly Ala Asp Asp Gln Val Gln Cys Phe Cys Gly Gly Lys Leu Lys
        195                 200                 205
Asn Trp Glu Pro Cys Asp Arg Ala Trp Ser Glu His Arg Arg His Phe
210                 215                 220
Pro Asn Cys Phe Phe Val Leu Gly Arg Asn Val Asn Val Arg Ser Glu
225                 230                 235                 240
Ser Gly Val Ser Ser Asp Arg Asn Phe Pro Asn Ser Thr Asn Ser Pro
                245                 250                 255
Arg Asn Pro Ala Met Ala Glu Tyr Glu Ala Arg Ile Val Thr Phe Gly
            260                 265                 270
Thr Trp Ile Tyr Ser Val Asn Lys Glu Gln Leu Ala Arg Ala Gly Phe
        275                 280                 285
Tyr Ala Leu Gly Glu Gly Asp Lys Val Lys Cys Phe His Cys Gly Gly
    290                 295                 300
Gly Leu Thr Asp Trp Lys Pro Ser Glu Asp Pro Trp Asp Gln His Ala
305                 310                 315                 320
Lys Cys Tyr Pro Gly Cys Lys Tyr Leu Leu Asp Glu Lys Gly Gln Glu
                325                 330                 335
Tyr Ile Asn Asn Ile His Leu Thr His Pro Leu Glu Glu Ser Leu Gly
            340                 345                 350
Arg Thr Ala Glu Lys Thr Pro Pro Leu Thr Lys Lys Ile Asp Asp Thr
        355                 360                 365
Ile Phe Gln Asn Pro Met Val Gln Glu Ala Ile Arg Met Gly Phe Ser
    370                 375                 380
Phe Lys Asp Leu Lys Lys Thr Met Glu Glu Lys Ile Gln Thr Ser Gly
385                 390                 395                 400
Ser Ser Tyr Leu Ser Leu Glu Val Leu Ile Ala Asp Leu Val Ser Ala
                405                 410                 415
Gln Lys Asp Asn Thr Glu Asp Glu Ser Ser Gln Thr Ser Leu Gln Lys
            420                 425                 430
Asp Ile Ser Thr Glu Glu Gln Leu Arg Arg Leu Gln Glu Glu Lys Leu
        435                 440                 445
Ser Lys Ile Cys Met Asp Arg Asn Ile Ala Ile Val Phe Phe Pro Cys
    450                 455                 460
Gly His Leu Ala Thr Cys Lys Gln Cys Ala Glu Ala Val Asp Lys Cys
465                 470                 475                 480
Pro Met Cys Tyr Thr Val Ile Thr Phe Asn Gln Lys Ile Phe Met Ser
                485                 490                 495
```

(2) INFORMATION FOR SEQ ID NO:11:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:11:

| Lys | Ala | Ala | Arg | Leu | Gly | Thr | Tyr | Thr | Asn | Trp | Pro | Val | Gln | Phe | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Glu Pro Ser Arg Met Ala Ala Ser Gly Phe Tyr Tyr Leu Gly Arg Gly
                20                  25                  30

Asp Glu Val Arg Cys Ala Phe Cys Lys Val Glu Ile Thr Asn Trp Val
            35                  40                  45

Arg Gly Asp Asp Pro Glu Thr Asp His Lys Arg Trp Ala Pro Gln Cys
        50                  55                  60

Pro Phe Val
65

(2) INFORMATION FOR SEQ ID NO:12:

(i) SEQUENCE CHARACTERISTICS:
      (A) LENGTH: 275 amino acids
      (B) TYPE: amino acid
      (C) STRANDEDNESS: Not Relevant
      (D) TOPOLOGY: both (ii) MOLECULE TYPE: protein (xi) SEQUENCE DESCRIPTION: SEQ ID NO:12:

Met Ser Asp Leu Arg Leu Glu Glu Val Arg Leu Asn Thr Phe Glu Lys
1               5                   10                  15

Trp Pro Val Ser Phe Leu Ser Pro Glu Thr Met Ala Lys Asn Gly Phe
                20                  25                  30

Tyr Tyr Leu Gly Arg Ser Asp Glu Val Arg Cys Ala Phe Cys Lys Val
            35                  40                  45

Glu Ile Met Arg Trp Lys Glu Gly Glu Asp Pro Ala Ala Asp His Lys
        50                  55                  60

Lys Trp Ala Pro Gln Cys Pro Phe Val Lys Gly Ile Asp Val Cys Gly
65                  70                  75                  80

Ser Ile Val Thr Thr Asn Asn Ile Gln Asn Thr Thr Thr His Asp Thr
                85                  90                  95

Ile Ile Gly Pro Ala His Pro Lys Tyr Ala His Glu Ala Ala Arg Val
                100                 105                 110

Lys Ser Phe His Asn Trp Pro Arg Cys Met Lys Gln Arg Pro Glu Gln
            115                 120                 125

Met Ala Asp Ala Gly Phe Phe Tyr Thr Gly Tyr Gly Asp Asn Thr Lys
        130                 135                 140

Cys Phe Tyr Cys Asp Gly Gly Leu Lys Asp Trp Glu Pro Glu Asp Val
145                 150                 155                 160

Pro Trp Glu Gln His Val Arg Trp Phe Asp Arg Cys Ala Tyr Val Gln
                165                 170                 175

Leu Val Lys Gly Arg Asp Tyr Val Gln Lys Val Ile Thr Glu Ala Cys
            180                 185                 190

Val Leu Pro Gly Glu Asn Thr Thr Val Ser Thr Ala Ala Pro Val Ser
        195                 200                 205

Glu Pro Ile Pro Glu Thr Lys Ile Glu Lys Glu Pro Gln Val Glu Asp
        210                 215                 220

Ser Lys Leu Cys Lys Ile Cys Tyr Val Glu Glu Cys Ile Val Cys Phe
225                 230                 235                 240

Val Pro Cys Gly His Val Val Ala Cys Ala Lys Cys Ala Leu Ser Val
                245                 250                 255

```
        Asp Lys Cys Pro Met Cys Arg Lys Ile Val Thr Ser Val Leu Lys Val
                        260                 265                 270

Tyr Phe Ser
                275

(2) INFORMATION FOR SEQ ID NO:13:

(i) SEQUENCE CHARACTERISTICS:
        (A) LENGTH: 498 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:13:

Met Thr Glu Leu Gly Met Glu Leu Glu Ser Val Arg Leu Ala Thr Phe
        1               5                   10                  15

Gly Glu Trp Pro Leu Asn Ala Pro Val Ser Ala Glu Asp Leu Val Ala
                        20                  25                  30

Asn Gly Phe Phe Ala Thr Gly Lys Trp Leu Glu Ala Glu Cys His Phe
                    35                  40                  45

Cys His Val Arg Ile Asp Arg Trp Glu Tyr Gly Asp Gln Val Ala Glu
                50                  55                  60

Arg His Arg Arg Ser Ser Pro Ile Cys Ser Met Val Leu Ala Pro Asn
        65                  70                  75                  80

His Cys Gly Asn Val Pro Arg Ser Gln Glu Ser Asp Asn Glu Gly Asn
                        85                  90                  95

Ser Val Val Asp Ser Pro Glu Ser Cys Ser Cys Pro Asp Leu Leu Leu
                        100                 105                 110

Glu Ala Asn Arg Leu Val Thr Phe Lys Asp Trp Pro Asn Pro Asn Ile
                    115                 120                 125

Thr Pro Gln Ala Leu Ala Lys Ala Gly Phe Tyr Tyr Leu Asn Arg Leu
                130                 135                 140

Asp His Val Lys Cys Val Trp Cys Asn Gly Val Ile Ala Lys Trp Glu
        145                 150                 155                 160

Lys Asn Asp Asn Ala Phe Glu Glu His Lys Arg Phe Phe Pro Gln Cys
                        165                 170                 175

Pro Arg Val Gln Met Gly Pro Leu Ile Glu Phe Ala Thr Gly Lys Asn
                        180                 185                 190

Leu Asp Glu Leu Gly Ile Gln Pro Thr Thr Leu Pro Leu Arg Pro Lys
                    195                 200                 205

Tyr Ala Cys Val Asp Ala Arg Leu Arg Thr Phe Thr Asp Trp Pro Ile
                210                 215                 220

Ser Asn Ile Gln Pro Ala Ser Ala Leu Ala Gln Ala Gly Leu Tyr Tyr
        225                 230                 235                 240

Gln Lys Ile Gly Asp Gln Val Arg Cys Phe His Cys Asn Ile Gly Leu
                        245                 250                 255

Arg Ser Trp Gln Lys Glu Asp Glu Pro Trp Phe Glu His Ala Lys Trp
                        260                 265                 270

Ser Pro Lys Cys Gln Phe Val Leu Leu Ala Lys Gly Pro Ala Tyr Val
                    275                 280                 285

Ser Glu Val Leu Ala Thr Thr Ala Ala Asn Ala Ser Ser Gln Pro Ala
                290                 295                 300

Thr Ala Pro Ala Pro Thr Leu Gln Ala Asp Val Leu Met Asp Glu Ala
        305                 310                 315                 320
```

```
Pro Ala Lys Glu Ala Leu Thr Leu Gly Ile Asp Gly Gly Val Val Arg
                325                 330                 335

Asn Ala Ile Gln Arg Lys Leu Leu Ser Ser Gly Cys Ala Phe Ser Thr
            340                 345                 350

Leu Asp Glu Leu Leu His Asp Ile Phe Asp Asp Ala Gly Ala Gly Ala
        355                 360                 365

Ala Leu Glu Val Arg Glu Pro Pro Glu Pro Ser Ala Pro Phe Ile Glu
    370                 375                 380

Pro Cys Gln Ala Thr Thr Ser Lys Ala Ala Ser Val Pro Ile Pro Val
385                 390                 395                 400

Ala Asp Ser Ile Pro Ala Lys Pro Gln Ala Ala Glu Ala Val Ser Asn
                405                 410                 415

Ile Ser Lys Ile Thr Asp Glu Ile Gln Lys Met Ser Val Ser Thr Pro
            420                 425                 430

Asn Gly Asn Leu Ser Leu Glu Glu Asn Arg Gln Leu Lys Asp Ala
        435                 440                 445

Arg Leu Cys Lys Val Cys Leu Asp Glu Glu Val Gly Val Val Phe Leu
    450                 455                 460

Pro Cys Gly His Leu Ala Thr Cys Asn Gln Cys Ala Pro Ser Val Ala
465                 470                 475                 480

Asn Cys Pro Met Cys Arg Ala Asp Ile Lys Gly Phe Val Arg Thr Phe
                485                 490                 495

Leu Ser
```

(2) INFORMATION FOR SEQ ID NO:14:

(i) SEQUENCE CHARACTERISTICS:
       (A) LENGTH: 67 amino acids
       (B) TYPE: amino acid
       (C) STRANDEDNESS: Not Relevant
       (D) TOPOLOGY: both (ii) MOLECULE TYPE: protein (xi) SEQUENCE DESCRIPTION: SEQ ID NO:14:

```
Glu Glu Val Arg Leu Asn Thr Phe Glu Lys Trp Pro Val Ser Phe Leu
1               5                   10                  15

Ser Pro Glu Thr Met Ala Lys Asn Gly Phe Tyr Tyr Leu Gly Arg Ser
            20                  25                  30

Asp Glu Val Arg Cys Ala Phe Cys Lys Val Glu Ile Met Arg Trp Lys
        35                  40                  45

Glu Gly Glu Asp Pro Ala Ala Asp His Lys Lys Trp Ala Pro Gln Cys
    50                  55                  60

Pro Phe Val
65
```

(2) INFORMATION FOR SEQ ID NO:15:

(i) SEQUENCE CHARACTERISTICS:
       (A) LENGTH: 67 amino acids
       (B) TYPE: amino acid
       (C) STRANDEDNESS: Not Relevant
       (D) TOPOLOGY: both (ii) MOLECULE TYPE: protein (xi) SEQUENCE DESCRIPTION: SEQ ID NO:15:

```
Glu Ala Asn Arg Leu Val Thr Phe Lys Asp Trp Pro Asn Pro Asn Ile
1               5                   10                  15

Thr Pro Gln Ala Leu Ala Lys Ala Gly Phe Tyr Tyr Leu Asn Arg Leu
```

```
              20                  25                  30
Asp His Val Lys Cys Val Trp Cys Asn Gly Val Ile Ala Lys Trp Glu
            35                  40                  45

Lys Asn Asp Asn Ala Phe Glu Glu His Lys Arg Phe Phe Pro Gln Cys
 50                  55                  60

Pro Arg Val
 65
```

(2) INFORMATION FOR SEQ ID NO:16:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:16:

```
Glu Phe Asn Arg Leu Lys Thr Phe Ala Asn Phe Pro Ser Ser Ser Pro
 1               5                  10                  15

Val Ser Ala Ser Thr Leu Ala Arg Ala Gly Phe Leu Tyr Thr Gly Glu
            20                  25                  30

Gly Asp Thr Val Gln Cys Phe Ser Cys His Ala Ala Ile Asp Arg Trp
            35                  40                  45

Gln Tyr Gly Asp Ser Ala Val Gly Arg His Arg Ile Ser Pro Asn
 50                  55                  60

Cys Arg Phe Ile
 65
```

(2) INFORMATION FOR SEQ ID NO:17:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:17:

```
Glu Phe Asn Arg Leu Lys Thr Phe Ala Asn Phe Pro Ser Gly Ser Pro
 1               5                  10                  15

Val Ser Ala Ser Thr Leu Ala Arg Ala Gly Phe Leu Tyr Thr Gly Glu
            20                  25                  30

Gly Asp Thr Val Arg Cys Phe Ser Cys His Ala Ala Val Asp Arg Trp
            35                  40                  45

Gln Tyr Gly Asp Ser Ala Val Gly Arg His Arg Lys Val Ser Pro Asn
 50                  55                  60

Cys Arg Phe Ile
 65
```

(2) INFORMATION FOR SEQ ID NO:18:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:18:

```
Glu Leu Tyr Arg Met Ser Thr Tyr Ser Thr Phe Pro Ala Gly Val Pro
1               5                   10                  15

Val Ser Glu Arg Ser Leu Ala Arg Ala Gly Phe Tyr Tyr Thr Gly Val
            20                  25                  30

Asn Asp Lys Val Lys Cys Phe Cys Cys Gly Leu Met Leu Asp Asn Trp
            35                  40                  45

Lys Arg Gly Asp Ser Pro Thr Glu Lys His Lys Lys Leu Tyr Pro Ser
50                  55                  60

Cys Arg Phe Val
65
```

(2) INFORMATION FOR SEQ ID NO:19:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:19:

```
Glu Leu Tyr Arg Met Ser Thr Tyr Ser Thr Phe Pro Ala Gly Val Pro
1               5                   10                  15

Val Ser Glu Arg Ser Leu Ala Arg Ala Gly Phe Tyr Tyr Thr Gly Val
            20                  25                  30

Asn Asp Lys Val Lys Cys Phe Cys Cys Gly Leu Met Leu Asp Asn Trp
            35                  40                  45

Lys Leu Gly Asp Ser Pro Ile Gln Lys His Lys Gln Leu Tyr Pro Ser
50                  55                  60

Cys Ser Phe Ile
65
```

(2) INFORMATION FOR SEQ ID NO:20:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:20:

```
Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ala
            20                  25                  30

Asp Asp Gln Val Gln Cys Phe Cys Cys Gly Gly Lys Leu Lys Asn Trp
            35                  40                  45

Glu Pro Cys Asp Arg Ala Trp Ser Glu His Arg Arg His Phe Pro Asn
50                  55                  60

Cys Phe Phe Val
65
```

(2) INFORMATION FOR SEQ ID NO:21:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both -continued

```
    (ii) MOLECULE TYPE: protein (xi) SEQUENCE DESCRIPTION: SEQ ID NO:21:

Glu Glu Ala Arg Leu Lys Ser Phe Gln Asn Trp Pro Asp Tyr Ala His
    1               5                   10                  15

Leu Thr Pro Arg Glu Leu Ala Ser Ala Gly Leu Tyr Tyr Thr Gly Ile
                    20                  25                  30

Gly Asp Gln Val Gln Cys Phe Cys Gly Gly Lys Leu Lys Asn Trp
                35                  40                  45

Glu Pro Cys Asp Arg Ala Trp Ser Glu His Arg His Phe Pro Asn
        50                  55                  60

Cys Phe Phe Val
    65

(2) INFORMATION FOR SEQ ID NO:22:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:22:

Glu Asn Ala Arg Leu Leu Thr Phe Gln Thr Trp Pro Leu Thr Phe Leu
    1               5                   10                  15

Ser Pro Thr Asp Leu Ala Arg Ala Gly Phe Tyr Tyr Ile Gly Pro Gly
                    20                  25                  30

Asp Arg Val Ala Cys Phe Ala Cys Gly Gly Lys Leu Ser Asn Trp Glu
                35                  40                  45

Pro Lys Asp Asn Ala Met Ser Glu His Leu Arg His Phe Pro Lys Cys
        50                  55                  60

Pro Phe Ile
    65

(2) INFORMATION FOR SEQ ID NO:23:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:23:

Glu Glu Ala Arg Phe Leu Thr Tyr His Met Trp Pro Leu Thr Phe Leu
    1               5                   10                  15

Ser Pro Ser Glu Leu Ala Arg Ala Gly Phe Tyr Tyr Ile Gly Pro Gly
                    20                  25                  30

Asp Arg Val Ala Cys Phe Ala Cys Gly Gly Lys Leu Ser Asn Trp Glu
                35                  40                  45

Pro Lys Asp Asp Ala Met Ser Glu His Arg Arg His Phe Pro Asn Cys
        50                  55                  60

Pro Phe Leu
    65

(2) INFORMATION FOR SEQ ID NO:24:

(i) SEQUENCE CHARACTERISTICS:
        (A) LENGTH: 66 amino acids
```

(B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:24:

Tyr Glu Ala Arg Ile Val Thr Phe Gly Thr Trp Ile Tyr Ser Val Asn
    1               5                   10                  15

Lys Glu Gln Leu Ala Arg Ala Gly Phe Tyr Ala Leu Gly Glu Gly Asp
                20                  25                  30

Lys Val Lys Cys Phe His Cys Gly Gly Gly Leu Thr Asp Trp Lys Pro
                35                  40                  45

Ser Glu Asp Pro Trp Asp Gln His Ala Lys Cys Tyr Pro Gly Cys Lys
        50                  55                  60

Tyr Leu
    65

(2) INFORMATION FOR SEQ ID NO:25:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:25:

Tyr Glu Ala Arg Ile Phe Thr Phe Gly Thr Trp Ile Tyr Ser Val Asn
    1               5                   10                  15

Lys Glu Gln Leu Ala Arg Ala Gly Phe Tyr Ala Leu Gly Glu Gly Asp
                20                  25                  30

Lys Val Lys Cys Phe His Cys Gly Gly Gly Leu Thr Asp Trp Lys Pro
                35                  40                  45

Ser Glu Asp Pro Trp Glu Gln His Ala Lys Trp Tyr Pro Gly Cys Lys
        50                  55                  60

Tyr Leu
    65

(2) INFORMATION FOR SEQ ID NO:26:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:26:

His Ala Ala Arg Phe Lys Thr Phe Phe Asn Trp Pro Ser Ser Val Leu
    1               5                   10                  15

Val Asn Pro Glu Gln Leu Ala Ser Ala Gly Phe Tyr Tyr Val Gly Asn
                20                  25                  30

Ser Asp Asp Val Lys Cys Phe Cys Cys Asp Gly Gly Leu Arg Cys Trp
                35                  40                  45

Glu Ser Gly Asp Asp Pro Trp Val Gln His Ala Lys Trp Phe Pro Arg
        50                  55                  60

Cys Glu Tyr Leu
    65

(2) INFORMATION FOR SEQ ID NO:27:

(i) SEQUENCE CHARACTERISTICS:
　　　　(A) LENGTH: 68 amino acids
　　　　(B) TYPE: amino acid
　　　　(C) STRANDEDNESS: Not Relevant
　　　　(D) TOPOLOGY: both (ii) MOLECULE TYPE: protein (xi) SEQUENCE DESCRIPTION: SEQ ID NO:27:

```
His Ala Ala Arg Met Arg Thr Phe Met Tyr Trp Pro Ser Ser Val Pro
 1               5                  10                  15

Val Gln Pro Glu Gln Leu Ala Ser Ala Gly Phe Tyr Tyr Val Gly Arg
                20                  25                  30

Asn Asp Asp Val Lys Cys Phe Gly Cys Asp Gly Gly Leu Arg Cys Trp
                35                  40                  45

Glu Ser Gly Asp Asp Pro Trp Val Glu His Ala Lys Trp Phe Pro Arg
        50                  55                  60

Cys Glu Phe Leu
        65
```

(2) INFORMATION FOR SEQ ID NO:28:

(i) SEQUENCE CHARACTERISTICS:
　　　　(A) LENGTH: 68 amino acids
　　　　(B) TYPE: amino acid
　　　　(C) STRANDEDNESS: Not Relevant
　　　　(D) TOPOLOGY: both (ii) MOLECULE TYPE: protein (xi) SEQUENCE DESCRIPTION: SEQ ID NO:28:

```
Glu Ala Ala Arg Leu Arg Thr Phe Ala Glu Trp Pro Arg Gly Leu Lys
 1               5                  10                  15

Gln Arg Pro Glu Glu Leu Ala Glu Ala Gly Phe Phe Tyr Thr Gly Gln
                20                  25                  30

Gly Asp Lys Thr Arg Cys Phe Cys Cys Asp Gly Gly Leu Lys Asp Trp
                35                  40                  45

Glu Pro Asp Asp Ala Pro Trp Gln Gln His Ala Arg Trp Tyr Asp Arg
        50                  55                  60

Cys Glu Tyr Val
        65
```

(2) INFORMATION FOR SEQ ID NO:29:

(i) SEQUENCE CHARACTERISTICS:
　　　　(A) LENGTH: 68 amino acids
　　　　(B) TYPE: amino acid
　　　　(C) STRANDEDNESS: Not Relevant
　　　　(D) TOPOLOGY: both (ii) MOLECULE TYPE: protein (xi) SEQUENCE DESCRIPTION: SEQ ID NO:29:

```
Glu Ala Ala Arg Val Lys Ser Phe His Asn Trp Pro Arg Cys Met Lys
 1               5                  10                  15

Gln Arg Pro Glu Gln Met Ala Asp Ala Gly Phe Phe Tyr Thr Gly Tyr
                20                  25                  30

Gly Asp Asn Thr Lys Cys Phe Tyr Cys Asp Gly Gly Leu Lys Asp Trp
                35                  40                  45

Glu Pro Glu Asp Val Pro Trp Glu Gln His Val Arg Trp Phe Asp Arg
        50                  55                  60
```

Cys Ala Tyr Val
65

(2) INFORMATION FOR SEQ ID NO:30:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:30:

Val Asp Ala Arg Leu Arg Thr Phe Thr Asp Trp Pro Ile Ser Asn Ile
1               5                   10                  15

Gln Pro Ala Ser Ala Leu Ala Gln Ala Gly Leu Tyr Tyr Gln Lys Ile
                20                  25                  30

Gly Asp Gln Val Arg Cys Phe His Cys Asn Ile Gly Leu Arg Ser Trp
            35                  40                  45

Gln Lys Glu Asp Glu Pro Trp Phe Glu His Ala Lys Trp Ser Pro Lys
        50                  55                  60

Cys Gln Phe Val
65

(2) INFORMATION FOR SEQ ID NO:31:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:31:

Glu Ser Val Arg Leu Ala Thr Phe Gly Glu Trp Pro Leu Asn Ala Pro
1               5                   10                  15

Val Ser Ala Glu Asp Leu Val Ala Asn Gly Phe Phe Gly Thr Trp Met
                20                  25                  30

Glu Ala Glu Cys Asp Phe Cys His Val Arg Ile Asp Arg Trp Glu Tyr
            35                  40                  45

Gly Asp Leu Val Ala Glu Arg His Arg Arg Ser Ser Pro Ile Cys Ser
        50                  55                  60

Met Val
65

(2) INFORMATION FOR SEQ ID NO:32:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:32:

Glu Gln Leu Arg Arg Leu Gln Glu Glu Arg Thr Cys Lys Val Cys Met
1               5                   10                  15

Asp Lys Glu Val Ser Val Val Phe Ile Pro Cys Gly His Leu Val Val
                20                  25                  30

Cys Gln Glu Cys Ala Pro Ser Leu Arg Lys Cys Pro Ile Cys
            35                  40                  45

(2) INFORMATION FOR SEQ ID NO:33:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:33:

```
Glu Gln Leu Arg Arg Leu Pro Glu Glu Arg Thr Cys Lys Val Cys Met
1               5                   10                  15

Asp Lys Glu Val Ser Ile Val Phe Ile Pro Cys Gly His Leu Val Val
            20                  25                  30

Cys Lys Asp Cys Ala Pro Ser Leu Arg Lys Cys Pro Ile Cys
        35                  40                  45
```

(2) INFORMATION FOR SEQ ID NO:34:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:34:

```
Glu Gln Leu Arg Arg Leu Gln Glu Glu Lys Leu Ser Lys Ile Cys Met
1               5                   10                  15

Asp Arg Asn Ile Ala Ile Val Phe Phe Pro Cys Gly His Leu Ala Thr
            20                  25                  30

Cys Lys Gln Cys Ala Glu Ala Val Asp Lys Cys Pro Met Cys
        35                  40                  45
```

(2) INFORMATION FOR SEQ ID NO:35:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:35:

```
Glu Gln Leu Arg Arg Leu Gln Glu Glu Lys Leu Cys Lys Ile Cys Met
1               5                   10                  15

Asp Arg Asn Ile Ala Ile Val Phe Val Pro Cys Gly His Leu Val Thr
            20                  25                  30

Cys Lys Gln Cys Ala Glu Ala Val Asp Lys Cys Pro Met Cys
        35                  40                  45
```

(2) INFORMATION FOR SEQ ID NO:36:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:36:

```
        Glu Glu Asn Arg Gln Leu Lys Asp Ala Arg Leu Cys Lys Val Cys Leu
        1               5                   10                  15

Asp Glu Glu Val Gly Val Val Phe Leu Pro Cys Gly His Leu Ala Thr
                        20                  25                  30

Cys Asn Gln Cys Ala Pro Ser Val Ala Asn Cys Pro Met Cys
                        35                  40                  45
```

(2) INFORMATION FOR SEQ ID NO:37:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:37:

```
        Glu Lys Glu Pro Gln Val Glu Asp Ser Lys Leu Cys Lys Ile Cys Tyr
        1               5                   10                  15

Val Glu Glu Cys Ile Val Cys Phe Val Pro Cys Gly His Val Val Ala
                        20                  25                  30

Cys Ala Lys Cys Ala Leu Ser Val Asp Lys Cys Pro Met Cys
                        35                  40                  45
```

(2) INFORMATION FOR SEQ ID NO:38:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:38:

```
        Ala Val Glu Ala Glu Val Ala Asp Asp Arg Leu Cys Lys Ile Cys Leu
        1               5                   10                  15

Gly Ala Glu Lys Thr Val Cys Phe Val Pro Cys Gly His Val Val Ala
                        20                  25                  30

Cys Gly Lys Cys Ala Ala Gly Val Thr Thr Cys Pro Val Cys
                        35                  40                  45
```

MAMMALIAN IAP ANTIBODIES AND DIAGNOSTIC KITS

BACKGROUND OF THE INVENTION

The invention relates to apoptosis.

There are two general ways by which cells die. An easily recognized pathway is necrosis, a process of cell death usually resulting from severe and sudden injury. In necrosis, changes in cellular homeostasis occur with loss of membrane integrity. Dysregulation of osmotic pressure results and cells swell and finally rupture. The cellular contents are then spilled into the surrounding tissue space and, usually, an inflammation response ensues. A second form of cell death is apoptosis. This cell "suicide" pathway or programmed cell death often occurs so rapidly that in some biological systems the apoptotic process is difficult to ascertain. Indeed, it has been only in the past few years that the involvement of apoptosis in a wide spectrum of biological processes has become recognized. Apoptosis is a fundamental physiological pathway of cell death, highly conserved throughout evolution, and playing a major role in development, viral pathogenesis, cancer, autoimmune diseases and neurodegenerative disorders.

Inappropriate increases in apoptosis may cause or contribute to a variety of diseases, including AIDS, neurodegenerative diseases (e.g. Alzheimer's Disease, Parkinson's Disease, Amyotrophic Lateral Sclerosis (ALS), retinitis pigmentosa and other diseases of the retina, myelodysplastic syndrome (e.g., aplastic anemia), toxin-induced liver disease (e.g., alcoholism) and ischemic injury (e.g., myocardial infarction, stroke, and reperfusion injury). In addition, disruption of normally occurring apoptosis has been implicated in the development of some cancers (e.g. follicular lymphoma, p53 carcinomas, and hormone dependent tumors), autoimmune disorders (e.g., lupus erythematosis and multiple sclerosis) and viral infections (e.g., herpes virus, poxvirus, and adenovirus infections).

Mature CD4$^+$T-lymphocytes in patients with HIV-1 have been observed to respond to stimulation with mitogens or super-antigens by undergoing increased apoptosis. The great majority of these cells are not infected and similar inappropriate antigen-induced apoptosis could be very important in the destruction of this vital part of the immune system early in HIV infection.

Baculoviruses encode inhibitors of apoptosis proteins (IAPs). These proteins inhibit the apoptosis which otherwise occurs when insect cells are infected by the virus. Baculovirus IAP proteins work in a manner which is thought to be independent of other viral proteins. The baculovirus IAP genes include sequences encoding a ring zinc finger-like motif which is presumed to be involved in the direct binding of DNA.

SUMMARY OF THE INVENTION

In general, the invention features substantially pure DNA (for example, genomic DNA, cDNA, or synthetic DNA) encoding a mammalian IAP polypeptide as defined below. In related aspects, the invention also features a vector, a cell (e.g., a mammalian, yeast or bacterial cell), and a transgenic animal or embryo thereof which includes such a substantially pure DNA encoding an IAP polypeptide.

In preferred embodiments, an IAP gene is the xiap (including m-xiap), hiap1, or the hiap2 gene. In most preferred embodiments the IAP gene is a human IAP gene. In other various preferred embodiments, the cell is a transformed cell. In related aspects, the invention features a transgenic animal containing a transgene which encodes an IAP polypeptide that is expressed in or delivered to tissue normally susceptible to apoptosis.

In yet another aspect, the invention features DNA encoding fragments of IAP polypeptides including the BIR domains and the RZF domains provided herein.

In another aspect, the invention features a DNA sequence substantially identical to the DNA sequence shown in FIG. 1.

In another aspect, the invention features a DNA sequence substantially identical to the DNA sequence shown in FIG. 2.

In another aspect, the invention features a DNA sequence substantially identical to the DNA sequence shown in FIG. 3.

In another aspect, the invention features a DNA sequence substantially identical to the DNA sequence shown in FIG. 4.

In another aspect, the invention also features RNA which is encoded by the DNA described herein. Preferably, the RNA is mRNA. In another embodiment the RNA is antisense RNA.

In another aspect, the invention features a substantially pure polypeptide having a sequence substantially identical to one of the IAP amino acid sequences shown in FIGS. 1–4.

In a second aspect, the invention features a substantially pure DNA which includes a promoter capable of expressing the IAP gene in a cell susceptible to apoptosis. In preferred embodiments, the IAP gene is xiap (including m-xiap), hiap1, or hiap2. hiap2 may be the full length gene, as shown in FIG. 3, or the truncated variant having the sequence boxed in FIG. 3 deleted.

In preferred embodiments, the promoter is the promoter native to an IAP gene. Additionally, transcriptional and translational regulatory regions are preferably native to an IAP gene.

The transgenic cells of the invention are preferably cells which are susceptible to apoptosis. In preferred embodiments the transgenic cell is a fibroblast, neuronal cell, a lymphocyte cell, or an insect cell. Most preferably, the neuron is a motor neuron and the lymphocyte is a CD4$^+$T-cell.

In another aspect, the invention features a method of inhibiting apoptosis which involves producing a transgenic cell having a transgene encoding an IAP polypeptide wherein the transgene is integrated into the genome of the cell and is positioned for expression in the cell wherein the IAP transgene is expressed in the cell at a level sufficient to inhibit apoptosis.

In another aspect, the invention features a method of detecting an IAP in a cell involving: (a) contacting the IAP gene or a portion thereof greater than 9 nucleic acids, preferably greater than 18 nucleic acids in length with a preparation of genomic DNA from the cell under hybridization conditions providing detection of DNA sequences having about 50% or greater nucleotide sequence identity to the amino acid encoding DNA sequences of hiap1, hiap2, or m-xiap IAP polypeptides.

In another aspect, the invention features a method of producing an IAP polypeptide which involves: (a) providing a cell transformed with DNA encoding an IAP polypeptide positioned for expression in the cell; (b) culturing the cell under conditions for expressing the DNA; and (c) isolating the IAP polypeptide. In preferred embodiments the IAP polypeptide is expressed by DNA which has a constituative or inducible promoter. In our embodiment, the promotor is a deterologous promoter.

In another aspect, the invention features substantially pure mammalian IAP polypeptide. Preferably, the polypeptide includes a greater than 50 amino acid sequence substantially identical to a greater than 50 amino acid sequence shown in any one of FIGS. 1–4. Most preferably, the polypeptide is the XIAP (including M-XIAP), HIAP1, or HIAP2 polypeptide. Fragments including BIR domains and RZF-domains provided herein are also a part of the invention.

In another aspect, the invention features a recombinant mammalian polypeptide capable of modulating apoptosis wherein the polypeptide includes at least a ring zinc finger domain and a BIR domain as defined herein. In preferred embodiments, the invention features a substantially pure polypeptide and an oligonucleotide encoding said polypeptide, the polypeptide including a ring zinc finger (RZF) having the sequence:

Glu Xaa1 Xaa1 Xaa1 Xaa1 Xaa1 Xaa1 Xaa2 Xaa1 Xaa1 Xaa1 Cys Lys Xaa3 Cys Met Xaa1 Xaa1 Xaa1 Xaa1 Xaa1 Xaa3 Xaa1 Phe Xaa1 Pro Cys Gly His Xaa1 Xaa1 Xaa1 Cys Xaa1 Xaa1 Cys Ala Xaa1 Xaa1 Xaa1 Xaa1 Xaa1 Cys Pro Xaa1 Cys, wherein Xaa1 is any amino acid, Xaa2 is Glu or Asp, Xaa3 is Val or Ile (SEQ ID NO:1);

and at least one BIR domain having the sequence: Xaa1 Xaa1 Xaa1 Arg Leu Xaa1 Thr Phe Xaa1 Xaa1 Trp Pro Xaa2 Xaa1 Xaa1 Xaa2 Xaa2 Xaa1 Xaa1 Xaa1 Xaa1 Leu Ala Xaa1 Ala Gly Phe Tyr Tyr Xaa1 Gly Xaa1 Xaa1 Asp Xaa1 Val Xaa1 Cys Phe Xaa1 Cys Xaa1 Xaa1 Xaa1 Xaa1 Xaa1 Xaa1 Trp Xaa1 Xaa1 Xaa1 Asp Xaa1 Xaa1 Xaa1 Xaa1 Xaa1 His Xaa1 Xaa1 Xaa1 Xaa1 Pro Xaa1 Cys Xaa1 Phe Val, wherein Xaa1 may be any amino acid and Xaa2 may be any amino acid or may be absent (SEQ ID NO:2).

In various preferred embodiments the protein has at least two or, more preferably at least three BIR domains, the RZF domain has one of the IAP sequences shown in FIG. 6, and the BIR domains are comprised of BIR domains shown in FIG. 5. In other preferred embodiments the BIR domains are at the amino terminal end of the protein relative to the RZF domain, which is at or near the carboxy terminus of the polypeptide.

In another aspect, the invention features an IAP gene isolated according to the method involving: (a) providing a sample of DNA; (b) providing a pair of oligonucleotides having sequence homology to a conserved region of an IAP disease-resistance gene; (c) combining the pair of oligonucleotides with the cell DNA sample under conditions suitable for polymerase chain reaction-mediated DNA amplification; and (d) isolating the amplified IAP gene or fragment thereof.

In preferred embodiments, the amplification is carried out using a reverse-transcription polymerase chain reaction, for example, the RACE method.

In another aspect, the invention features an IAP gene isolated according to the method involving: (a) providing a preparation of DNA; (b) providing a detectably-labelled DNA sequence having homology to a conserved region of an IAP gene; (c) contacting the preparation of DNA with the detectably-labelled DNA sequence under hybridization conditions providing detection of genes having 50% or greater nucleotide sequence identity; and (d) identifying an IAP gene by its association with the detectable label.

In another aspect, the invention features an IAP gene isolated according to the method involving: (a) providing a cell sample; (b) introducing by transformation into the cell sample a candidate IAP gene; (c) expressing the candidate IAP gene within the cell sample; and (d) determining whether the cell sample exhibits an altered apoptotic response, whereby a response identifies an IAP gene.

In another aspect, the invention features a method of identifying an IAP gene in a cell, involving: (a) providing a preparation of cellular DNA (for example, from the human genome or a cDNA library (such as a cDNA library isolated from a cell type which undergoes apoptosis); (b) providing a detectably-labelled DNA sequence (for example, prepared by the methods of the invention) having homology to a conserved region of an IAP gene; (c) contacting the preparation of cellular DNA with the detectably-labelled DNA sequence under hybridization conditions providing detection of genes having 50% nucleotide or greater sequence identity; and (d) identifying an IAP gene by its association with the detectable label.

In another aspect, the invention features a method of isolating an IAP gene from a recombinant library, involving: (a) providing a recombinant library; (b) contacting the library with a detectably-labelled gene fragment produced according to the PCR method of the invention under hybridization conditions providing detection of genes having 50% or greater nucleotide sequence identity; and (c) isolating an IAP gene by its association with the detectable label.

In another aspect, the invention features a method of identifying an IAP gene involving: (a) providing a cell tissue sample; (b) introducing by transformation into the cell sample a candidate IAP gene; (c) expressing the candidate IAP gene within the cell sample; and (d) determining whether the cell sample exhibits inhibition of apoptosis, whereby a change in (i.e. modulation of) apoptosis identifies an IAP gene.

Preferably, the cell sample is a cell type which may be assayed for apoptosis (e.g., lymphocytes, T-cells and B-cells, neuronal cells, baculovirus infected insect cells and fibroblast cells); the candidate IAP gene is obtained from a cDNA expression library; and the apoptosis response is the inhibition of apoptosis.

In another aspect, the invention features a method of inhibiting apoptosis in a mammal wherein the method includes: (a) providing DNA encoding at least one IAP polypeptide to a cell which is susceptible to apoptosis; wherein the DNA is integrated into the genome of the cell and is positioned for expression in the cell; and the IAP gene is under the control of regulatory sequences suitable for controlled expression of the gene(s); wherein the IAP transgene is expressed at a level sufficient to inhibit apoptosis relative to a cell lacking the IAP transgene. It will be appreciated that IAP polypeptides also may be administered directly to inhibit any undesirable apoptosis.

In a related aspect, the invention features a method of inhibiting apoptosis wherein the method involves: (a) producing a cell having integrated in the genome a transgene containing the IAP gene under the control of a promoter providing constitutive expression of the IAP gene.

In yet another related aspect, the invention features a method of inhibiting apoptosis wherein the method involves: (a) producing a cell having integrated in the genome a transgene containing the IAP gene under the control of a promoter providing controllable expression of the IAP gene; and (b) regulating the environment of the cell so that the IAP transgene is controllably expressed in the cell. In preferred embodiments, the IAP gene is expressed using a tissue-specific or cell type-specific promoter, or by a promoter that is activated by the introduction of an external signal or agent, such as a chemical signal or agent. In preferred embodiments the cell is a lymphocyte or B-cell, a neuronal cell, or a fibroblast. In other embodiments the cell is a cell in an HIV infected human, or a mammal with a neurodegenerative disease, ischemia, toxin induced liver disease, or a myelodysplastic syndrome.

In a related aspect, the invention provides a method of inhibiting apoptosis in a mammal by providing an apoptosis-inhibiting amount of IAP polypeptide.

In another aspect, the invention features a purified antibody which binds specifically to an IAP family protein. Such an antibody may be used in any standard immunodetection method for the identification of an IAP polypeptide. Preferably, the antibody binds specifically to xiap, hiap1 or hiap2. In various embodiments the antibody may react with other IAP polypeptides or may be specific for one or a few IAP polypeptides. The antibody may be a monoclonal or polyclonal antibody.

In another aspect, the invention features a method of identifying a compound which modulates apoptosis. The method includes (a) providing a cell expressing an IAP polypeptide; and (b) contracting the cell with a candidate compound, and monitoring the expression of an IAP gene. An alteration in the level of expression of the IAP gene indicates the presence of a compound which modulates apoptosis. The compound may be an inhibitor or an enhancer of apoptosis. In various preferred embodiments, the cell is a fibroblast, a neuronal cell, a lymphocyte (T-cell or B-cell), or an insect cell; the polypeptide expression being monitored is XIAP (e.g., human or murine), HIAP1, or HIAP2.

By "IAP gene" is meant a gene encoding a polypeptide having at least one BIR domain and a ring zinc finger domain which is capable of modulating (inhibiting or enhancing) apoptosis in a cell or tissue when provided by other intracellular or extracellular delivery methods. In preferred embodiments the IAP gene is a gene having about 50% or greater nucleotide sequence identity to at least one of the IAP amino acid encoding sequences of FIGS. 1–4 or portions thereof. Preferably, the region of sequence over which identity is measured is a region encoding at least one BIR domain and a ring zinc finger domain. Mammalian IAP genes include nucleotide sequences isolated from any mammalian source. Preferably, the mammal is a human.

By an "IAP gene" is also meant any member of the family of apoptosis inhibitory genes characterized by their ability to modulate apoptosis and having at least 20%, preferably 30%, and most preferably 50% amino acid sequence identity to at least one of the conserved regions of one of the IAP members described herein (i.e., either the BIR or ring zinc finger domains from xiap, hiap1 and hiap2, or m-xiap). Representative members of the IAP gene family include, without limitation, the xiap, hiap1, and hiap2 genes of humans, and the m-xiap gene of the mouse. By "IAP protein" is meant a polypeptide encoded by an IAP gene.

By "BIR domain" is meant a domain having the amino acid sequence of the consensus sequence: Xaa1 Xaa1 Xaa1 Arg Leu Xaa1 Thr Phe Xaa1 Xaa1 Trp Pro Xaa2 Xaa1 Xaa1 Xaa2 Xaa2 Xaa1 Xaa1 Xaa1 Leu Ala Xaa1 Ala Gly Phe Tyr Tyr Xaa1 Gly Xaa1 Xaa1 Asp Xaa1 Val Xaa1 Cys Phe Xaa1 Cys Xaa1 Xaa1 Xaa1 Xaa1 Xaa1 Xaa1 Trp Xaa1 Xaa1 Xaa1 Asp Xaa1 Xaa1 Xaa1 Xaa1 Xaa1 His Xaa1 Xaa1 Xaa1 Xaa1 Pro Xaa1 Cys Xaa1 Phe Val, wherein Xaa1 is any amino acid and Xaa2 is any amino acid or is absent (SEQ ID NO:2). Preferably, the sequence is substantially identical to one of the BIR domain sequences provided for xiap, hiap1, hiap2 or m-xiap herein.

By "ring zinc finger" or "RZF" is meant a domain having the amino acid sequence of the consensus sequence: Glu Xaa1 Xaa1 Xaa1 Xaa1 Xaa1 Xaa1 Xaa2 Xaa1 Xaa1 Xaa1 Cys Lys Xaa3 Cys Met Xaa1 Xaa1 Xaa1 Xaa1 Xaa1 Xaa3 Xaa1 Phe Xaa1 Pro Cys Gly His Xaa1 Xaa1 Xaa1 Cys Xaa1 Xaa1 Cys Ala Xaa1 Xaa1 Xaa1 Xaa1 Xaa1 Cys Pro Xaa1 Cys, wherein Xaa1 is any amino acid, Xaa2 is Glu or Asp, and Xaa3 is Val or Ile (SEQ ID NO:1). Preferably, the sequence is substantially identical to the RZF domains provided herein for xiap (including m-xiap), hiap1, hiap2.

By "modulating apoptosis" or "altering apoptosis" is meant increasing or decreasing the number of cells which undergo apoptosis in a given cell population. Preferably, the cell population is selected from a group including T-cells, neuronal cells, fibroblasts, or any other cell line known to undergo apoptosis in a laboratory setting (e.g., the baculovirus infected insect cells). It will be appreciated that the degree of modulation provided by an IAP or modulating compound in a given assay will vary, but that one skilled in the art can determine the statistically significant change in the level of apoptosis which identifies an IAP or a compound which modulates an IAP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By a "substantially pure polypeptide" is meant an IAP polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, IAP polypeptide. A substantially pure IAP polypeptide may be obtained, for example, by extraction from a natural source (e.g., a fibroblast, neuronal cell, or lymphocyte cell); by expression of a recombinant nucleic acid encoding an IAP polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an IAP polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome.

By "transformation" is meant any method for introducing foreign molecules into a cell. Lipofection, calcium phosphate precipitation, retroviral deliver, electroporation and biolistic transformation are just a few of the teachings which may be used. For example, Biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., an IAP polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "conserved region" is meant any stretch of six or more contiguous amino acids exhibiting at least 30%, preferably 50%, and most preferably 70% amino acid sequence identity between two or more of the IAP family members, (e.g., human HIAP1, HIAP2, and XIAP). Examples of preferred conserved regions are shown (as boxed or designated sequences) in FIGS. 5–7 and Tables 1 and 2, and include, without limitation, BIR domains and ring zinc finger domains.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., an IAP specific antibody. A purified antibody may be obtained, for example, by affinity chromatography using recombinantly-produced protein or conserved motif peptides and standard techniques.

By "specifically binds" is meant an antibody which recognizes and binds a protein but which does not substantially recognize and bind other molecules in a sample, e.g., a biological sample, which naturally includes protein.

Other features and advantages of the invention will be apparent from the following description of the preferred embodiments thereof, and from the claims.

DETAILED DESCRIPTION

The drawings will first be described.

Drawings

FIG. 1 is the human xiap cDNA sequence and the XIAP polypeptide sequence (SEQ ID NOS:3,4).

FIG. 2 is the human hiap1 cDNA sequence and the HIAP1 polypeptide sequence (SEQ ID NOS:5,6).

FIG. 3 is the human hiap2 cDNA sequence and the HIAP2 polypeptide sequence (SEQ ID NOS:7,8). The sequence absent in the hiap2-G variant is boxed.

FIG. 4 is the m-xiap cDNA sequence and XIAP polypeptide sequence (SEQ ID NOS:9,10).

FIG. 5 shows the alignment of the BIR domains of IAP proteins (SEQ ID NOS:11 and 14–31).

FIG. 6 is the alignment of human IAP polypeptides with diap, cp-iap, and the consensus sequence (SEQ ID NOS:4, 6, 8, 10, 12, and 13).

FIG. 7 shows the alignment of the Ring Zinc Finger domains of IAP proteins (SEQ ID NOS:32–38).

I. IAP Polypeptides and Genes Encoding IAP Polypeptides

We have discovered a new class of mammalian proteins which modulate apoptosis (IAPs) and the genes which encode these proteins. The IAP proteins are characterized by the presence of a ring zinc finger (RZF) domain (FIG. 7) and at least one BIR domain as defined by the boxed consensus sequences in FIGS. 5 and 6 and by the sequence domains provided in Tables 1 and 2. As examples of the IAP proteins we provide the cDNA sequences and amino acid sequences for these new human apoptosis inhibitors, HIAP1, HIAP2, and XIAP and a new murine modulator, XIAP. Additional members of the mammalian IAP family may be isolated using standard cloning techniques and the conserved amino acid sequences, primers and probes provided herein and known in the art.

TABLE 1

NUCLEOTIDE POSITION OF CONSERVED DOMAINS*

|  | BIR-1 | BIR-2 | BIR-3 | Ring Zinc Finger |
| --- | --- | --- | --- | --- |
| Xiap | 109–312 | 520–723 | 826–1023 | 1348–1485 |
| m-Xiap | 202–405 | 613–816 | 916–1113 | 1438–1575 |
| hiap1 | 273–476 | 693–893 | 951–1154 | 1824–1961 |
| hiap2 | 373–576 | 787–987 | 1042–1245 | 1915–2052 |

*Positions indicate correspond to those shown in FIGS. 1–4.

TABLE 2

AMINO ACID POSITION OF CONSERVED DOMAINS*

|  | BIR-1 | BIR-2 | BIR-3 | Ring Zinc Finger |
| --- | --- | --- | --- | --- |
| Xiap | 26–93 | 163–230 | 265–330 | 439–484 |
| m-Xiap | 26–93 | 163–230 | 264–329 | 438–483 |
| hiap1 | 29–96 | 169–234 | 255–322 | 546–591 |
| hiap2 | 46–113 | 184–250 | 269–336 | 560–605 |

*Positions indicate correspond to those shown in FIGS. 1–4.

Recognition of this mammalian IAP family has provided emergent patterns of protein structure. Recognition of these patterns has also allowed us assign the function of a modulator of apoptosis to a drosophila gene product of previously unknown function (Genbank Accession Number M96581). The amino acid sequence of this protein, termed diap, is shown in FIG. 6 for comparison.

The IAP proteins may be used to inhibit the apoptosis which occurs as part of disease or disorder processes. For example, IAP polypeptides or nucleic acid encoding IAP polypeptides may be administered for the treatment of or prevention of apoptosis which occurs as a part of AIDS, neurodegenerative diseases, ischemic injury, toxin-induced liver disease and myelodysplastic syndromes. Nucleic acid encoding the IAP polypeptide may also be provided to inhibit apoptosis.

II. Cloning of IAP Genes

A. XIAP

Figure 10:
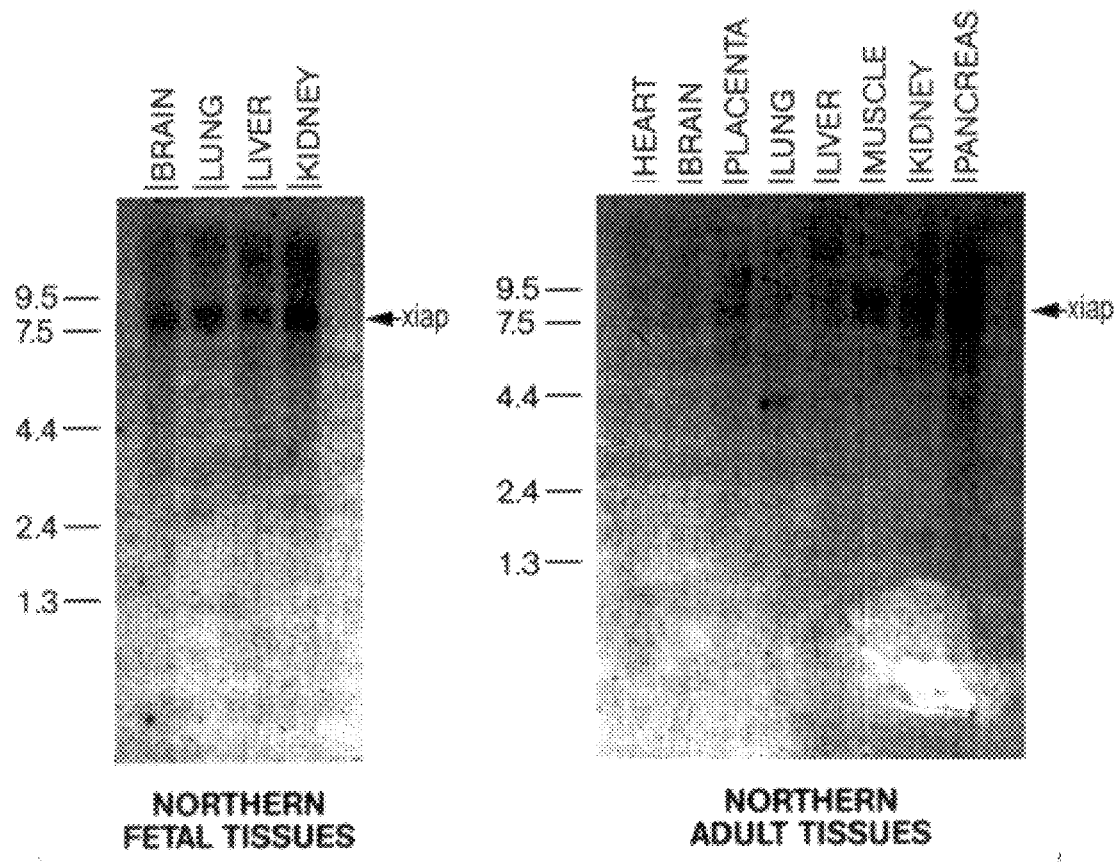
FIG. 10 are Northern blots showing human xiap mRNA expression in human tissues.

Our search for human genes potentially involved in apoptosis has resulted in the identification of an x-linked sequence tag site (STS) in the GenBank which demonstrated strong homology with the conserved RZF domain of CpIAP and OpIAP, the two baculovirus genes known to inhibit apoptosis (Clem et al., Mol. Cell Biol., 14:5212–5222, (1994); and Birnbaum et al, J. Virol. 68:2521–8, (1994)). Screening a human fetal brain ZapII cDNA library (Stratagene, La Jolla, Calif.) with this STS resulted in the identification and cloning of xiap (for X-linked Inhibitor of apoptosis protein gene). The human gene has a 1.7 kb coding sequence that includes three BIR (baculovirus inhibitor of apoptosis repeat (Crook et al., J. Virol. 67:2168–74, (1993), Clem et al., Science 254:1388–90, (1991); and Birnbaum et al., J. Virol., 68:2521–8, (1994)) domains and a zinc finger. Northern analysis with xiap reveals a greater than 7 kb message expressed in different tissues particularly liver and kidney (FIG. 10). The large size of the transcript reflects large 5' and 3' untranslated regions.

B. HIAP1 and HIAP2

Figure 8:
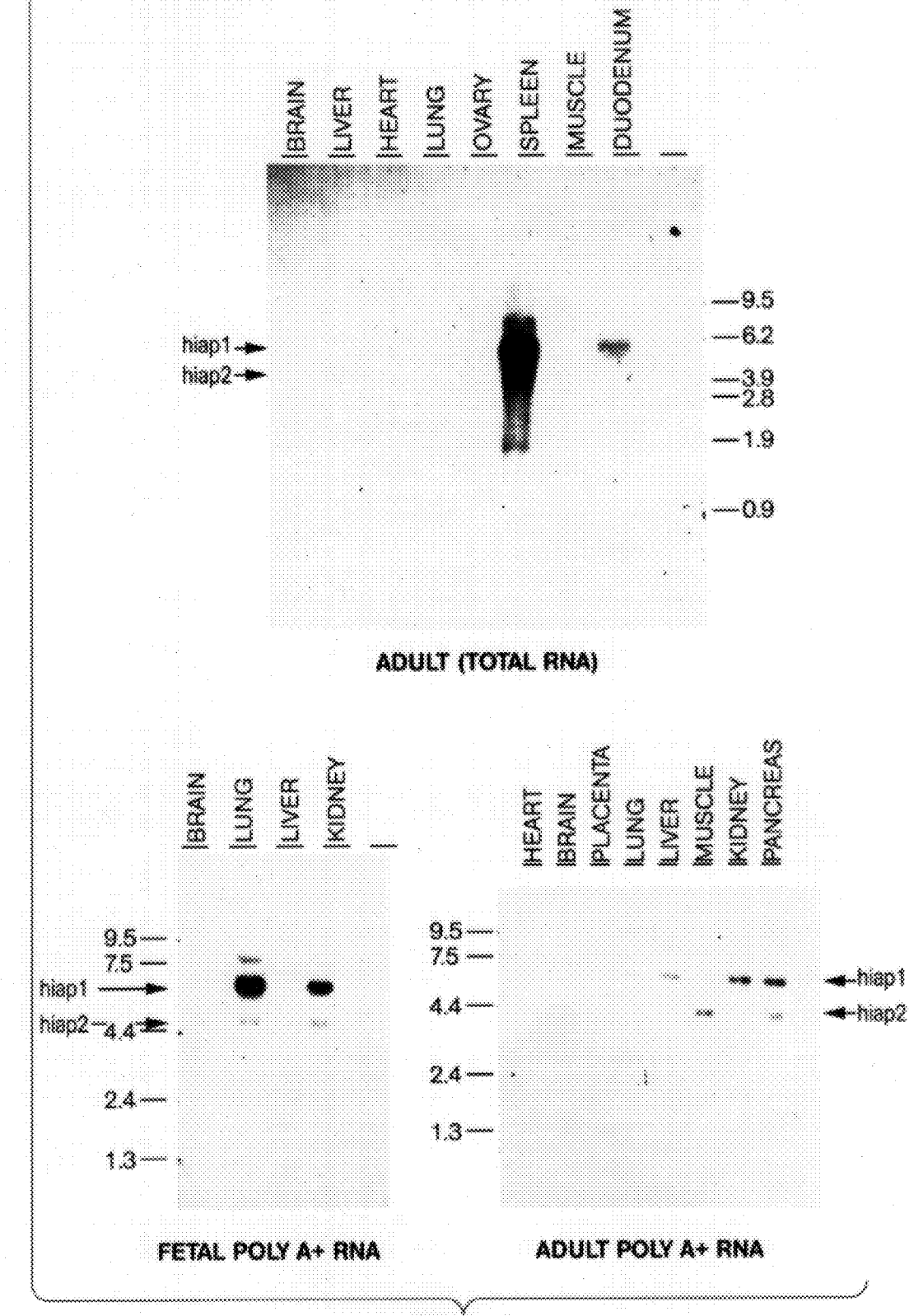
FIG. 8 are Northern blots showing human hiap1 and hiap2 mRNA expression in human tissues.
Figure 9:
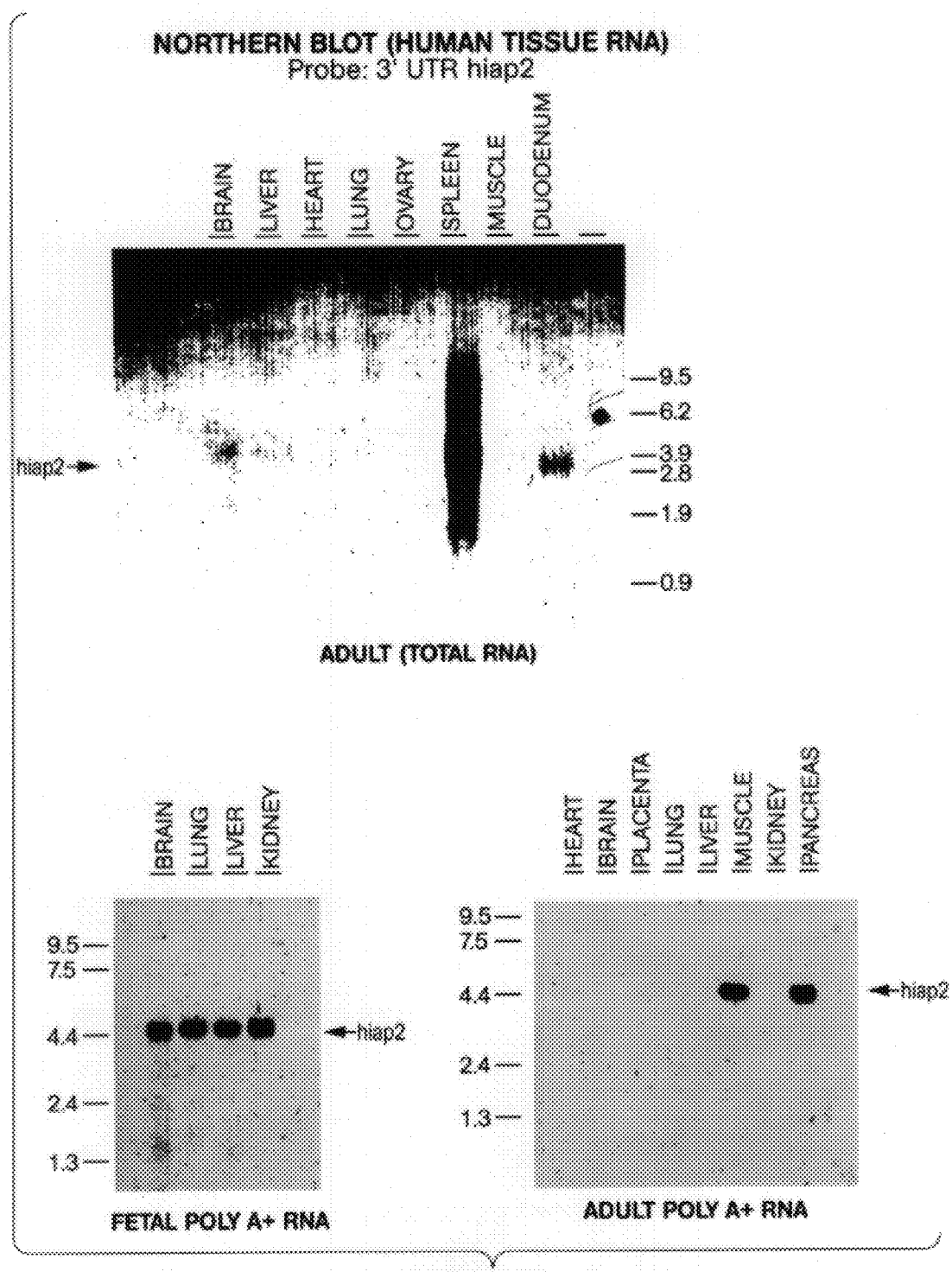
FIG. 9 are Northern blots showing human hiap2 mRNA expression in human tissues.

The hiap1 and hiap2 genes were cloned by screening a human liver library (Stratagene) with a probe including the whole xiap coding region at low stringency (40° C. wash, 2×ssc, 10% SDS) (FIGS. 2 and 3). hiap1 and hiap2 were also independently detected using a probe derived from a expressed sequence tag (EST) (GenBank Accession No. T96284) which includes a portion of a BIR domain. This EST was originally isolated by the PCR amplification of a cDNA library using the EST-specific primers. The derived probe was then used to screen the human liver cDNA library for full length hiap coding sequences. We have subsequently detected a third DNA which includes the hiap2 sequence which appears to lack one exon, presumably due to alternative mRNA splicing (see boxed region in FIG. 3). FIGS. 8 and 9 show hiap1 and hiap2 expression in human tissues as assayed by Northern Analysis.

C. M-XIAP

Screening of a mouse embryo λgt11 cDNA library (Clonetech, Palo Alto, Calif.) and a mouse FIX II genomic library with a xiap cDNA clones probe has resulted in the identification of 14 positive cDNA and two hybridizing genomic clones. A cDNA contig spanning 8.0 kb was constructed using 12 overlapping mouse clones. DNA sequencing revealed a coding sequence of about 1.7 kb. The mouse gene called m-xiap (for mouse x-linked inhibitor of apoptosis protein gene) shows striking amino acid homology with xiap at and around the initiation methionine, the stop codon, the three BIR domains and the zinc finger domain. As with the human gene, the mouse homologue contains large 5' and 3' UTRs predicted to result in a transcript as large as 7–8 kb.

Sequencing and restriction mapping of m-xiap can be used to further delineate the structure and genomic organization of m-xiap. Southern blot analysis and inverse PCR technique (Groden et al., Cell 66:589–600 (1991) can be employed to map exons and sequence exon-intron boundaries.

Antisera can be raised against a m-xiap fusion protein expressed in *Escherichia coli* using a bacterial expression system. The resulting antisera can be used along with Northern blot analysis to analyze the spatial and temporal expression of m-xiap in the mouse.

III. Cloning of Addition IAP Genes

Low stringency Southern blot hybridization of human genomic using probes specific for xiap, hiap1 and hiap2 show bands which correspond to the other known human IAP sequences. In addition, these probes detect sequences which do not correspond to known IAP sequences. This result indicates that additional IAP sequences may be readily identified using low stringency hybridization. xiap, hiap1, hiap2, and m-xiap specific primers which may be used to clone additional genes by RT PCR are shown in Table 3. Standard techniques including PCR and hybridization may be used to clone homologs and additional genes.

IV. Characterization of IAP Apoptosis Modulating Activity

The apoptosis inhibiting capability of IAPs can be defined in an in vitro system know to detect alterations in apoptosis. Mammalian expression constructs carrying IAPs and their truncated forms can be introduced into various cell lines such as CHO, HIH 3T3, HL60, Rat-1, or Jurkart cells, for example. In addition, SF21 insect cells may be used in which case the IAP gene is preferentially expressed using an insect heat shock promotor. Apoptosis will then be induced in transfected cells and controls employing standard methodologies (e.g. serum withdrawal and staurosporine). A survival index (ratio of surviving transfected cells to surviving control cells) will indicate the strength of each IAP construct in inhibiting apoptosis. These experiments can confirm the presence of apoptosis inhibiting or enhancing activity and, can help to determine the minimal functional region of an IAP. These methods may also be used in combination with compounds to identify compounds which modulate apoptosis via their effect on IAP expression.

Specific examples of apoptosis assays are provided in the following references:

Lymphocyte: C. J. Li et al., "Induction of apoptosis in uninfected lymphocytes by HIV-1 Tat protein", Science, 268:429–431 (1995); D. Gibellini et al., "Tat-expressing Jurkat cells show an increased resistance to different apoptotic stimuli, including acute human immunodeficiency virus-type 1 (HIV-1) infection", Br. J. Haematol. 89:24–33, (1995); S. J. Martin et al., "HIV-1 infection of human CD4+ T cells in vitro. Differential induction of apoptosis in these cells." J. Immunol. 152:330–42, (1994); C. Terai et al., "Apoptosis as a mechanism of cell death in cultured T lymphoblasts acutely infected with HIV-1", J. Clin Invest., 87:1710–5, (1991); J. Dhein et al., "Autocrine T-cell suicide mediated by APO-1/(Fas/CD95)", Nature 373:438–441, (1995); P. D. Katsikis et al., "Fas antigen stimulation induces marked apoptosis of T lymphocytes in human immunodeficiency virus-infected individuals", J. Exp. Med. 1815:2029–2036, (1995); Michael O. Westendorp et al., Sensitization of T cells to CD95-mediated apoptosis by HIV-1 Tat and gp120", Nature, 375:497, (1995); DeRossi et al., Virology 198:234–44, (1994).

Fibroblasts: H. Vossbeck et al., "Direct transforming activity of TGF-beta on rat fibroblasts", Int. J. Cancer, 61:92–97, (1995); S. Goruppi et al., "Dissection of c-myc domains involved in S phase induction of NIH3T3 fibroblasts", Oncogene, 9:1537–44, (1994); A. Fernandez et al., "Differential sensitivity of normal and Ha-ras-transformed C3H mouse embryo fibroblasts to tumor necrosis factor: induction of bcl-2, c-myc, and manganese superoxide dismutase in resistant cells", Oncogene, 9:2009–17, (1994); E. A. Harrington et al., "c-Myc-induced apoptosis in fibroblasts in inhibited by specific cytokines", Embo J., 13:3286–3295, (1994); N. Itoh et al., "A novel protein domain required for apoptosis. Mutational analysis of human Fas antigen", J. Biol. Chem., 268:10932–7, (1993).

Neuronal Cells: G. Melino et al., "Tissue transglutaminase and apoptosis: sense and antisense transfection studies with human neuroblastoma cells", Mol. Cell. Biol., 14:6584–6596, (1994); D. M. Rosenbaum et al., "Evidence for hypoxia-induced, programmed cell death of cultured neurons", Ann. Neurol., 36:864–870, (1994); N. Sato et al., "Neuronal differentiation of PC12 cells as a result of prevention of cell death by bcl-2", J. Neurobiol, 25:1227–1234, (1994); G. Ferrari et al., "N-acetylcysteine (D- and L-stereoisomers) prevents apoptotic death of neuronal cells", J. Neurosci., 1516:2857–2866, (1995); A. K. Talley et al., "Tumor necrosis factor alpha-induced apoptosis in human neuronal cells: protection by the antioxidant N-acetylcysteine and the genes bcl-2 and crmA", Mol. Cell Biol., 1585:2359–2366, (1995); A. K. Talley et al., "Tumor Necrosis Factor Alpha-Induced Apoptosis in Human Neuronal Cells: Protection by the Antioxidant N-Acetylcysteine and the Genes bcl-2 and crmA", Mol. and Cell. Biol., 15:2359–2366, (1995); G. Walkinshaw et al., "Induction of apoptosis in catecholaminergic PC12 cells by L-DOPA. Implications for the treatment of Parkinson's disease.", J. Clin. Invest. 95:2458–2464, (1995).

Insect Cells: R. J. Clem et al., "Prevention of apoptosis by a baculovirus gene during infection of insect cells", Science, 254:1388–90, (1991); N. E. Crook et al., "An apoptosis-inhibiting baculovirus gene with a zinc finger-like motif", J. Virol., 67:2168–74, (1993); S. Rabizadeh et al., "Expression of the baculovirus p35 gene inhibits mammalian neural cell death", J. Neurochem., 61:2318–21, (1993); M. J. Birnbaum et al., "An apoptosis-inhibiting gene from a nuclear polyhedrosis virus encoding a polypeptide with Cys/His sequence motifs", J. Virol, 68:2521–8, (1994); R. J. Clem et al., "Control of programmed cell death by the baculovirus genes p35 and iap", Mol. Cell. Biol., 14:5212–5222, (1994).

V. Construction of a Transgenic Mammal

Characterization of IAPs can provide information that allows for the development of an IAP knockout mouse model by homologous recombination (or an IAP over producing mouse by other means of integration). A replacement type targeting vector can be constructed using an isogenic genomic clone from a mouse strain, e.g. 129/Sv (Strategene LaJolla, Calif.). The targeting vector will be introduced into a J1 line of embryonic stem (ES) cells by electroporation to generate ES cell lines that carry a profoundly truncated form of an IAP. To generate chimeric founder mice, the targeted cell lines will be injected into a mouse blastula stage embryo. Heterozygote offspring will be interbred to homozygosity. Knockout mice may be constructed as a means of screening in vivo for therapeutic compounds which modulate apoptosis.

VI. IAP Protein Expression

IAP genes may be expressed in both prokaryotic and eukaryotic cell types. For those IAP's which increase apoptosis it may be desirable to express the protein under control of an inducible promotor for the purposes of protein production.

In general, IAP proteins according to the invention may be produced by transformation of a suitable host cell with all or part of a IAP-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The IAP protein may be produced in a prokaryotic host (e.g., *E. coli*) or in a eukaryotic host (e.g., *Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, N. Y., 1994). The method of transformation or transfection and the choice of expression vehicle will depend on the host system selected. Transformation and transfection methods are described, e.g., in Ausubel et al., (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Pal Alto, Calif.). If desired, this system may be used in conjunction with other protein expression techniques, for example, the myc tag approach described by Evan et al. (Mol. Cell Biol. 5:3610–3616, 1985).

Alternatively, a IAP protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the IAP protein is cloned into an expression vector which includes the dihydrofolate reductase (DHFR) gene. Integration of the plasmid and, therefore, the IAP protein-encoding gene into the host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻cells, ATCC Accession No. CRL 9096) are among the host cells preferred for DHFR selection of a stably-transfected cell line or DHFR-mediated gene amplification.

Once the recombinant IAP protein is expressed, it is isolated, e.g., using affinity chromatography. In one example, an anti-IAP protein antibody (e.g., produced as described herein) may be attached to a column and used to isolate the IAP protein. Lysis and fractionation of IAP protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short IAP protein fragments, can also be produced by chemical synthesis (e.g., by the methods described in *Solid Phase Peptide Synthesis* , 2nd ed., 1984 The Pierce Chemical Co., Rockford, Ill.).

These general techniques of polypeptide expression and purification can also be used to produce and isolate useful IAP fragments or analogs (described herein).

VI. Anti-IAP Antibodies

To generate IAP-specific antibodies, a IAP coding sequence (i.e., amino acids 180–276) can be expressed as a C-terminal fusion with glutathione S-transferase (GST) (Smith et al., Gene 67:31–40, 1988). The fusion protein can be purified on glutathione-Sepharose beads, eluted with glutathione cleaved with thrombin (at the engineered cleavage site), and purified to the degree necessary for immunization of rabbits. Primary immunizations can be carried out with Freund's complete adjuvant and subsequent immunizations with Freund's incomplete adjuvant. Antibody titres are monitored by Western blot and immunoprecipitation analyses using the thrombin-cleaved IAP protein fragment of the GST-IAP fusion protein. Immune sera are affinity purified using CNBr-Sepharose-coupled IAP protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of IAP may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using IAP expressed as a GST fusion protein.

Alternatively, monoclonal antibodies may be prepared using the IAP proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific IAP recognition by Western blot or immunoprecipitation analysis (by the methods described in Ausubel et al., supra). Antibodies which specifically recognize IAP are considered to be useful in the invention; such antibodies may be used, e.g., in an immunoassay to monitor the level of IAP produced by a mammal (for example, to determine the amount or subcellular location of IAP).

Preferably, antibodies of the invention are produced using fragments of the IAP protein which lie outside highly conserved regions and appear likely to be antigenic, by criteria such as those provided by the Peptide structure program of the Genetics Computer Group Sequence Analysis Package (Program Manual for the GCG Package, Version 7, 1991) using the algorithm of Jameson and Wolf (CABIOS 4:181 1988)). Specifically these regions, which are found between BIR1 and BIR2 of all the IAP proteins, are in hiap1 from amino acid 99 to 170, hiap2 from amino acid 123 to 184, xiap from 116 to 133 and m-xiap from 116 to 133. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

VII. Identification of Molecules that Modulate IAP Protein Expression

Isolation of the IAP cDNAs also facilitates the identification of molecules which increase or decrease IAP expression. According to one approach, candidate molecules are added at varying concentrations to the culture medium of cells expressing IAP mRNA. IAP expression is then measured, for example, by standard Northern blot analysis (Ausubel et al., supra) using a IAP cDNA (or cDNA fragment) as a hybridization probe (see also Table III). The level of IAP expression in the presence of the candidate molecule is compared to the level measured for the same cells in the same culture medium but in the absence of the candidate molecule.

If desired, the effect of candidate modulators on expression may, in the alternative, be measured at the level of IAP protein production using the same general approach and standard immunological detection techniques, such as Western blotting or immunoprecipitation with a IAP-specific antibody (for example, the IAP antibody described herein).

Candidate modulators may be purified (or substantially purified) molecules or may be one component of a mixture of compounds (e.g., an extract or supernatant obtained from cells; Ausubel et al., supra). In a mixed compound assay, IAP expression is tested against progressively smaller subsets of the candidate compound pool (e.g., produced by standard purification techniques, e.g., HPLC or FPLC) until a single compound or minimal compound mixture is demonstrated to modulate IAP expression.

Alternatively, or in addition, candidate compounds may be screened for those which modulate IAP apoptosis inhibiting activity. In this approach, the degree of apoptosis in the presence of a candidate compound is compared to the degree of apoptosis in its absence, under equivalent conditions. Again, such a screen may begin with a pool of candidate compounds, from which one or more useful modulator compounds are isolated in a step-wise fashion. Apoptosis activity may be measured by any standard assay, for example, those described herein.

Candidate IAP modulators include peptide as well as non-peptide molecules (e.g., peptide or non-peptide molecules found, e.g., in a cell extract, mammalian serum, or growth medium on which mammalian cells have been cultured).

A molecule which promotes an increase in IAP expression or IAP activity is considered particularly useful in the invention; such a molecule may be used, for example, as a therapeutic to increase cellular levels of IAP and thereby exploit the effect of IAP polypeptides for the inhibition of apoptosis.

Modulators found to be effective at the level of IAP expression or activity may be confirmed as useful in animal models and, if successful, may be used as anti-cancer therapeutics for either the inhibition or the enhancement of apoptosis, as appropriate.

IX. IAP Therapy

Because expression levels of IAP genes correlates with the levels of apoptosis, the IAP gene also finds use in anti-apoptosis gene therapy. In particular, to sustain neuronal cells, lymphocytes (T-cells and B-cells), or cells exposed to ischemic injury, a functional IAP gene may be introduced into cells at the sites predicted to undergo undesirable apoptosis.

Retroviral vectors, adenoviral vectors, adeno-associated viral vectors, or other viral vectors with the appropriate tropism for cells likely to be involved in apoptosis (for example, epithelial cells) may be used as a gene transfer delivery system for a therapeutic IAP gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259:988–990, 1993; and Johnson, Chest 107:77S–83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches may also be employed for the introduction of therapeutic DNA into cells otherwise predicted to undergo apoptosis. For example, IAP may be introduced into a neuronal cell or a T-cell by the techniques of lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic IAP DNA construct is preferably applied to the site of the predicted apoptosis event (for example, by injection), but may also be applied to tissue in the vicinity of the predicted apoptosis event or even to a blood vessel supplying the cells predicted to undergo apoptosis.

In the gene therapy constructs, IAP cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in neural cells or T-cells may be used to direct IAP expression. Such enhancers include, without limitation, those enhancers which are characterized as tissue or cell specific in their expression.

Alternatively, if a IAP genomic clone is utilized as a therapeutic construct (for example, following its isolation by hybridization with the IAP cDNA described above), IAP expression is regulated by its cognate regulatory sequences or, if desired, by regulatory sequences derived from a heterologous source, e.g., any of the promoters or regulatory elements described above.

Less preferably, IAP gene therapy is accomplished by direct administration of the IAP mRNA to a cell predicted to undergo apoptosis. This mRNA may be produced and isolated by any standard technique, but is most readily produced by in vitro transcription using a IAP cDNA under the control of a high efficiency promoter (e.g., the T7 promoter). Administration of IAP mRNA to malignant cells is carried out by any of the methods for direct nucleic acid administration described above.

Ideally, the production of IAP protein by any gene therapy approach described above results in a cellular level of IAP that is at least equivalent to the normal, cellular level of IAP in an unaffected individual. Treatment by any IAP-mediated gene therapy approach may be combined with more traditional therapies.

Another therapeutic approach included within the invention involves direct administration of recombinant IAP protein, either to the site of a predicted apoptosis event (for example, by injection) or systemically by any conventional recombinant protein administration technique. The actual dosage of IAP depends on a number of factors, including the size and health of the individual patient, but, generally, between 0.1 mg and 100 mg inclusive are administered per day to an adult in any pharmaceutically-acceptable formulation.

X. Administration of IAP Polypeptides, IAP Genes, or Modulators of IAP Synthesis or Function A IAP protein, gene, or modulator may be administered with a pharmaceutically-acceptable diluent, carrier, or excipient, in unit dosage form. Conventional pharmaceutical practice may be employed to provide suitable formulations or compositions to administer IAP to patients suffering from or presymptomatic for a IAP-associated carcinoma. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a IAP protein, gene, or modulatory compound may be combined with more traditional therapies for the disease such as surgery, radiation, or chemotherapy for cancers; surgery, steroid therapy, and chemotherapy for autoimmune diseases; antiviral therapies for AIDS; and for example, TPA for ischemic injury.

XI. Detection of a Condition Involving Altered Apoptosis

IAP polypeptides and nucleic acid sequences find diagnostic use in the detection or monitoring of conditions involving aberrant levels of apoptosis. For example, decrease expression of IAP may be correlated with enhanced apoptosis in humans (see XII, below). Accordingly, a decrease or increase in the level of IAP production may provide an indication of a deleterious condition. Levels of IAP expression may be assayed by any standard technique. For example, its expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H. A. Ehrlich, Stockton Press, N.Y.; and Yap and McGee, Nucl. Acids. Res. 19:4294, 1991).

Alternatively, a patient sample may be analyzed for one or more mutations in the IAP sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant IAP detection, and each is well known in the art; examples of particular techniques are described, without limitation, in Orita et al., Proc. Natl. Acad. Sci. USA 86:2766–2770 , (1989) and Sheffield et al., Proc. Natl. Acad. Sci. USA 86:232–236, (1989).

In yet another approach, immunoassays are used to detect or monitor IAP protein in a biological sample. IAP-specific polyclonal or monoclonal antibodies (produced as described above) may be used in any standard immunoassay format (e.g., ELISA, Western blot, or RIA assay) to measure IAP polypeptide levels; again comparison is to wild-type IAP levels, and a decrease in IAP production is indicative of a condition involving increased apoptosis. Examples of immunoassays are described, e.g., in Ausubel et al., supra. Immunohistochemical techniques may also be utilized for IAP detection. For example, a tissue sample may be obtained from a patient, and a section stained for the presence of IAP using an anti-IAP antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of IAP protein production (for example, by immunological techniques or the protein truncation test (Hogerrorst, F.B.L., et al., Nature Genetics 10:208–212 (1995) and also includes a nucleic acid-based detection technique designed to identify more subtle IAP mutations (for example, point mutations). As described above, a number of mismatch detection assays are available to those skilled in the art, and any preferred technique may be used (see above). By this approach, mutations in IAP may be detected that either result in loss of IAP expression or loss of IAP biological activity. In a variation of this combined diagnostic method, IAP biological activity is measured as protease activity using any appropriate protease assay system (for example, those described above).

Mismatch detection assays also provide the opportunity to diagnose a IAP-mediated predisposition to diseases of apoptosis. For example, a patient heterozygous for an IAP mutation may show no clinical symptoms and yet possess a higher than normal probability of developing one or more types of neurodegenerative, myelodysplastic or ischemic diseases. Given this diagnosis, a patient may take precautions to minimize their exposure to adverse environmental factors (for example, UV exposure or chemical mutagens) and to carefully monitor their medical condition (for example, through frequent physical examinations). This type of IAP diagnostic approach may also be used to detect IAP mutations in prenatal screens.

The IAP diagnostic assays described above may be carried out using any biological sample (for example, any biopsy sample or bodily fluid or tissue) in which IAP is normally expressed (for example, the inhibition of apoptosis). Identification of a mutant IAP gene may also be assayed using these sources for test samples. Alternatively, a IAP mutation, particularly as part of a diagnosis for predisposition to IAP-associated degenerative disease, may be tested using a DNA sample from any cell, for example, by mismatch detection techniques; preferably, the DNA sample is subjected to PCR amplification prior to analysis.

XII. Treatment of HIV Infected Individuals

We have found that hiap1 and hiap2 expression is decreased significantly in HIV infected human cells. This decrease preceeds apoptosis. The result indicates that administration of HIAP1, HIAP2, genes encoding these proteins, or compounds which upregulate these genes can be used to prevent T-cell attrition in HIV infected patients. The following assay may also be used to screen for compounds which alter hiap1 and hiap2 expression and which also prevent apoptosis.

The experiments were preformed as follows: Cultured mature lymphocyte CD-4+ T-cell lines (H9 labelled "a"; CEM/CM-3 labelled "b"; 6T-CEM labelled "c"; and Jurkat labelled "d" in FIGS. 11A and 11B) were examined for apoptosis (FIG. 11A) and hiap gene expression (Fig. 11B). Control conditions are labelled as lane 1 in FIG. 11A and Fig. 11B. Lane 2 shows the result 24 hours after PHA/PMH (phytohemagglutinin, phorbol ester) mitogen stimulation. Lane 3 shows the result 24 hours after HIV strain $III_B$ infection. The "M" refers to standard DNA markers, the 123 bp ladder (Gibco-BRL) in Fig. 11B, and lambda HindIII ladder (Gibco-BRL) in Fig. A.

Figure 11A:
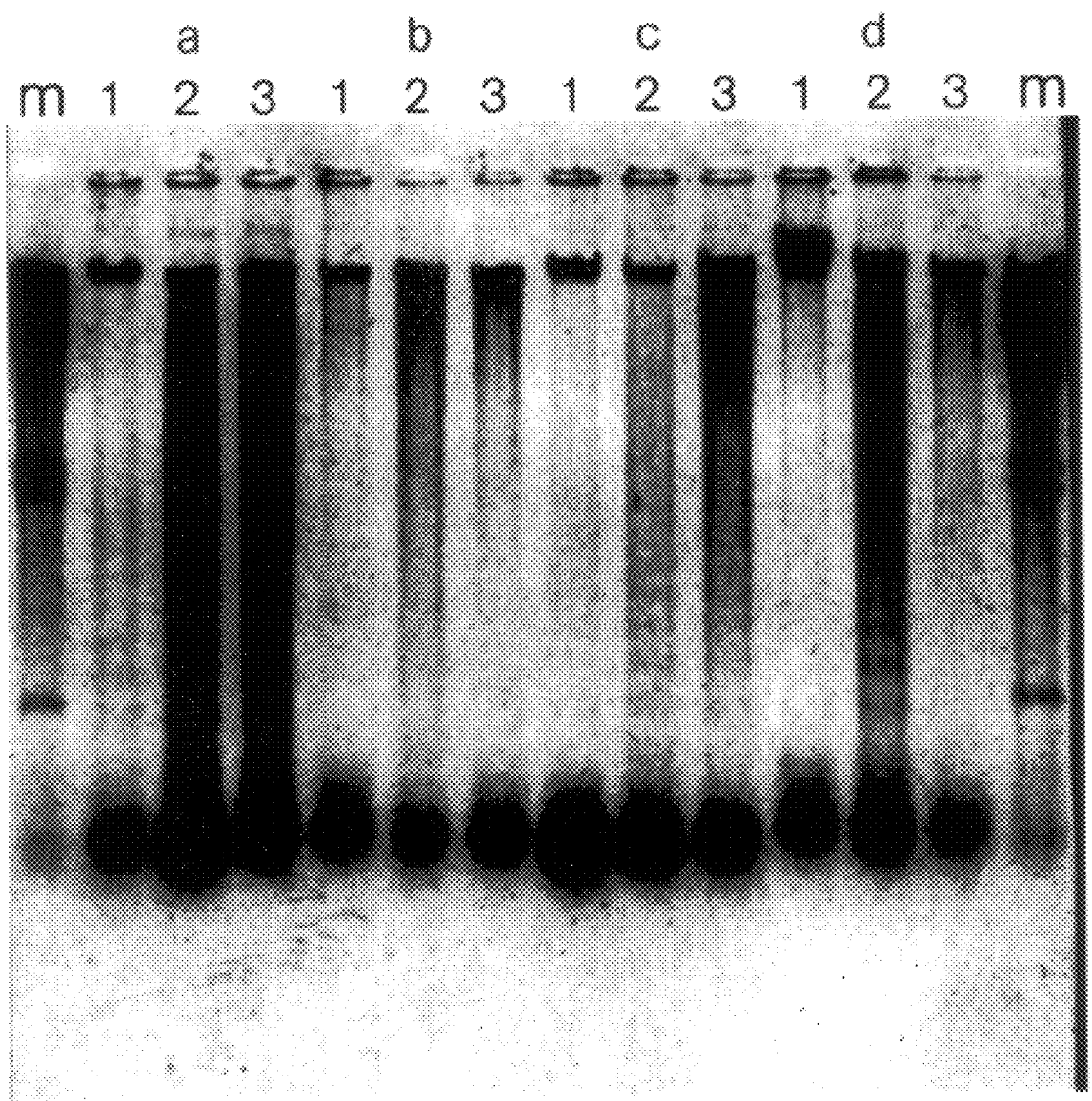
FIGS. 11A and 11B are agarose gels showing apoptic DNA ladders and RT PCR products using hiap1 and hiap2 specific probes in HIV infected T cells.
Figure 11B:
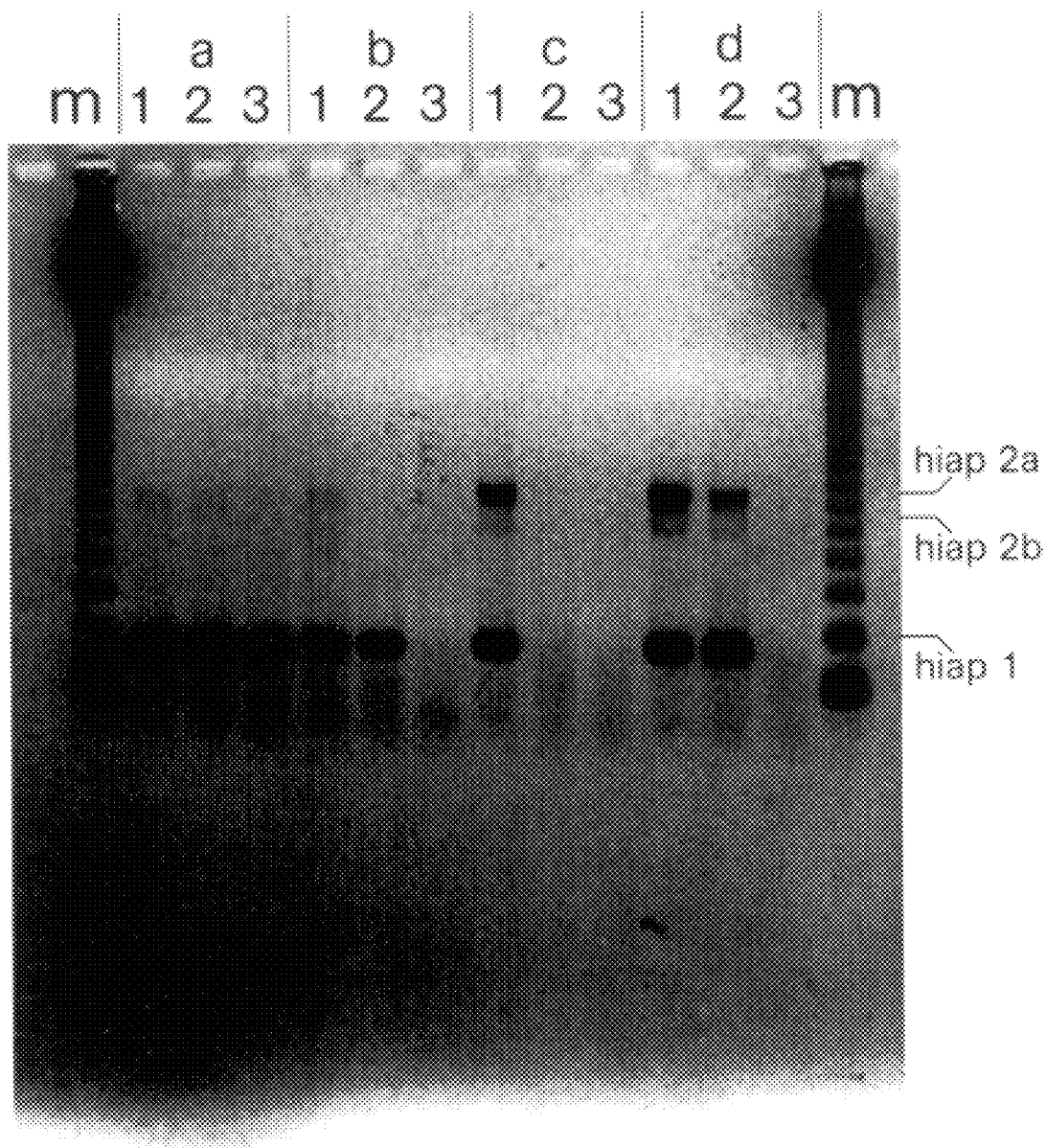

In FIG. 11A is a picture of ethidium bromide stained gel showing the presenced of DNA ladders (as assayed by the test of Prigent et al., J. of Immun. Methods, 160:139–140, (1993), indicative of apoptosis. The sensitivity and degree of apoptosis of the four T-cell lines varies following mitogen stimulation and HIV infection.

For the experiment examining hiap gene expression, total RNA was prepared from the cultured cells and subject to a reverse transcriptase reaction using oligo-dT priming. The RT cDNA products were PCR amplified using specific primers (as shown in Table III) for the detection of hiap2a, hiap2b and hiap1. PCR conditions were routine (94° C. melting for 1 minute, 55° C. annealing for 2 minutes and 72° C. extension for 1.5 minutes for 35 cycles) using a Perkin-Elmer 480 thermocycler. The Fig. 11B shows a picture of the RT-PCR products run on a 1% agarose gel stained with ethidium bromide. Absence of hiap2 transcripts is noted in all four cell lines 24 hours after HIV infection. In three of four cell lines (all except H9), the hiap1 gene is also dramatically down-regulated after HIV infection. PHA/PMA mitogen stimulation also appears to decrease hiap gene expression, particularly for hiap2 and to a lesser extent, for hiap1.

The data from these experiments is summarized in the accompanying Table 4. The β-action gene expression was consistent in all cell lines tested, indicating that a flow in the RT-PCR assay does not account for the decreases in hiap gene expression.

TABLE 3

Oligonucleotide primers for the specific RT-PCR amplification of unique IAP genes

| IAP Gene | Forward Primer (nucleotide position*) | Reverse Primer (nucleotide position*) | Size of Product (bp) |
| --- | --- | --- | --- |
| Xiap | p2415 (876–896) | p2449 (1291–1311) | 435 |
| m-xiap | p2566 (458–478) | p2490 (994–1013) | 555 |
| hiap 1 | p2465 (827–847) | p2464 (1008–1038) | 211 |
| hiap 2 | p2595 (1562–1585) | p2578 (2339–2363) | 801[a] 618[b] |

*Nucleotide position as determined from FIGS. 1–4 for each IAP gene
[a]PCR product size of hiap2a
[b]PCR product size of hiap2b

TABLE 4

Apoptosis and hiap gene expression in cultured T-cells following mitogen stimulation or HIV infection

| Cell Line | Condition | Apoptosis | hiap1 | hiap2 |
| --- | --- | --- | --- | --- |
| H9 | not stimulated | – | + | +/– |
|  | PHA/PMA stimulated | +++ | + | +/– |
|  | HIV infected | ++ | + | – |
| CEM/CM-3 | not stimulated | – | + | +/– |
|  | PHA/PMA stimulated | +/– | + | – |
|  | HIV infected | +/– | – | – |
| 6T-CEM | not stimulated | – | + | + |
|  | PHA/PMA stimulated | +/– | – | – |
|  | HIV infected | + | – | – |
| Jurkat | not stimulated | – | + | ++ |
|  | PHA/PMA stimulated | + | + | + |
|  | HIV infected | +/– | – | – |

XIII. Preventive Anti-Apoptotic Therapy

In a patient diagnosed to be heterozygous for an IAP mutation or to be susceptible to IAP mutations (even if those mutations do not yet result in alteration or loss of IAP biological activity), or a patent diagnosed as HIV positive, any of the above therapies may be administered before the occurrence of the disease phenotype. For example, the therapies may be provided to a patient who is HIV positive but does not yet show a diminished T-cell count or other signs of full-blown AIDS. In particular, compounds shown to increase IAP expression or IAP biological activity may be administered by any standard dosage and route of administration (see above). Alternatively, gene therapy using an IAP expression construct may be undertaken to reverse or prevent the cell defect prior to the development of the degenerative disease.

The methods of the instant invention may be used to reduce or diagnose the disorders described herein in any mammal, for example, humans, domestic pets, or livestock. Where a non-human mammal is treated or diagnosed, the IAP polypeptide, nucleic acid, or antibody employed is preferably specific for that species.

Other Embodiments

In other embodiments, the invention includes any protein which is substantially identical to a mammalian IAP polypeptides (FIGS. 1–4; SEQ ID NO:1–4); such homologs include other substantially pure naturally-occurring mammalian IAP proteins as well as allelic variants; natural mutants; induced mutants; DNA sequences which encode proteins and also hybridize to the IAP DNA sequences of FIGS. 1–4 (SEQ ID NOS:1–4) under high stringency conditions or, less preferably, under low stringency conditions (e.g., washing at 2xSSC at 40° C. with a probe length of at least 40 nucleotides); and proteins specifically bound by antisera directed to a IAP polypeptide. The term also includes chimeric polypeptides that include a IAP portion.

The invention further includes analogs of any naturally-occurring IAP polypeptide. Analogs can differ from the naturally-occurring IAP protein by amino acid sequence differences, by post-translational modifications, or by both. Analogs of the invention will generally exhibit at least 85%, more preferably 90%, and most preferably 95% or even 99% identity with all or part of a naturally-occurring IAP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring IAP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes IAP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of IAP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a IAP nucleic acid or amino acid sequence in a sample to be diagnosed. Particularly useful IAP fragments for this purpose include, without limitation, the amino acid fragments shown in Table 2.

All publications and patent applications mentioned in this specification are herein incorporated by reference to the same extent as if each independent publication or patent application was specifically and individually indicated to be incorporated by reference.

What is claimed is:

1. A purified antibody which specifically binds to a mammalian IAP family protein said mammalian IAP family protein having a ring zinc finger domain contained within the protein.

2. A kit for testing a mammal for the presence or an apoptosis disease or an increased likelihood of developing an apoptosis disease, said kit comprising a substantially pure antibody that specifically binds to a mammalian IAP polypeptide said mammalian IAP protein having a ring zinc finger domain contained within the protein.

3. The kit of claim 2, said kit further comprising a means for detecting said binding of said antibody to said mammalian IAP polypeptide.

4. The antibody of claim 1, wherein said mammal is a human.

5. The antibody of claim 1, wherein said mammal is a mouse.

6. The antibody of claim 1, wherein said IAP is HIAP-1.

7. The antibody of claim 1, wherein said IAP is HIAP-2.

8. The antibody of claim 1, wherein said IAP is XIAP.

9. The kit of claim 2, wherein said mammal is a human.

10. The kit of claim 2, wherein said mammal is a mouse.

11. The kit of claim 2, wherein said IAP is HIAP-1.

12. The kit of claim 2, wherein said IAP is HIAP-2.

13. The kit of claim 2, wherein said IAP is XIAP.

14. The kit of claim 2, wherein said disease is a proliferative disease.

15. The kit of claim 2, wherein said disease is a neurodegenerative disease.

16. The kit of claim 2, wherein said disease is a disease of the retina.

17. The kit of claim 2, wherein said disease is a myelodysplastic syndrome.

18. The kit of claim 2, wherein said disease is toxin-induced liver disease.

19. The kit of claim 2, wherein said disease is ischemic injury.

20. The kit of claim 2, wherein said disease is cancer.

21. The kit of claim 2, wherein said disease is an autoimmune disorder.

22. The kit of claim 2, wherein said disease is viral infection.

23. The antibody of claim 1, wherein said antibody is a polyclonal antibody.

24. The antibody of claim 1, wherein said antibody is a monoclonal antibody.

25. The kit of claim 2, wherein said antibody is a polyclonal antibody.

26. The kit of claim 2, wherein said antibody is a monoclonal antibody.

* * * * *

UNITED STATES PATENT AND TRADEMARK OFFICE
CERTIFICATE OF CORRECTION

PATENT NO.   : 5,919,912                                                      Page 1 of 1
DATED        : July 6, 1999
INVENTOR(S)  : Robert G. Korneluk, Alexander E. MacKenzie and Stephen Baird It is certified that error appears in the above-identified patent and that said Letters Patent is hereby corrected as shown below:

Column 8,
Line 64, "FIG. 8" should be -- FIG. 8A-8C --
Line 66, "FIG. 9" should be -- FIG. 9A-9C --

Column 9,
Line 1, "FIG. 10" should be -- FIG. 10A and 10B --

Signed and Sealed this

First Day of October, 2002

Attest:

Attesting Officer

JAMES E. ROGAN
Director of the United States Patent and Trademark Office